(12) United States Patent
Fulton et al.

(10) Patent No.: US 7,736,898 B1
(45) Date of Patent: Jun. 15, 2010

(54) THIAMINASES AND THIAMINASE GENES FOR USE IN APOPTOTIC THERAPIES

(75) Inventors: Chandler Fulton, Weston, MA (US); Elaine Y. Lai, Weston, MA (US)

(73) Assignee: Brandeis University, Waltham, MA (US)

( * ) Notice: Subject to any disclaimer, the term of this patent is extended or adjusted under 35 U.S.C. 154(b) by 0 days.

(21) Appl. No.: 09/675,509

(22) Filed: Sep. 29, 2000

Related U.S. Application Data

(60) Provisional application No. 60/156,952, filed on Sep. 29, 1999, provisional application No. 60/087,526, filed on Jun. 1, 1998, provisional application No. 60/052,377, filed on Jul. 11, 1997.

(51) Int. Cl.
*C12N 15/74* (2006.01)
*C12N 5/00* (2006.01)
*C12N 5/02* (2006.01)
*C12N 15/00* (2006.01)
*A61K 48/00* (2006.01)
*A01N 63/00* (2006.01)
*C07H 21/02* (2006.01)

(52) U.S. Cl. .................. 435/471; 435/325; 435/455; 435/320.1; 424/93.21; 424/93.4; 536/23.1

(58) Field of Classification Search .............. 800/3, 800/8, 9, 11, 13, 18; 514/44; 424/93.21, 424/93.4; 435/325, 455, 471, 320.1; 536/23.1
See application file for complete search history.

(56) References Cited

U.S. PATENT DOCUMENTS 5,646,008 A    7/1997    Thompson et al.

OTHER PUBLICATIONS

Palu et.al.; In pursuit of new developments for gene therapy of human diseases, 1999, Journal of Biotechnology 68: 1-13.*
Romano et al.; Latest Developments in Gene Transfer Technology: Achievements, Perspectives, and Controversies over Therapeutic Applications, 2000, Stem Cells, 18: 19-39.*
Eck et. al.; Gene-Based Therapy, 1996, Pharmacological Basis of Therapeutics: 77-101.*
"*Salmonella.*" Encyclopædia Britannica 2003 Encyclopædia Britannica Online. Jan, 30, 2003 <http://www.search.eb.com/eb/article?eu=66793>.*
"*Clostridium.*" Encyclopædia Britannica 2003 Encyclopædia Britannica Online. Jan. 30, 2003 http://www.search.eb.com/eb/article?eu=24827.*
"genetic engineering". (2007). In Encyclopædia Britannica. Retrieved Jan. 21, 2007, from Encyclopædia Britannica Online: http://www.search.eb.com/eb/article-9036395.*
Current Protocols in Molecular Biology, (2002), Section 1.1-1.03 and 1.51-1.5.17 (John Wiley and Sons).*

\* cited by examiner

*Primary Examiner*—Thaian N Ton
(74) *Attorney, Agent, or Firm*—Foley & Lardner LLP

(57) ABSTRACT

This disclosure describes methods for preparing and utilizing thiaminase and thiaminase genes to induce apoptosis in a selected group of vertebrate cells in vivo by reducing the level of thiamin in the cells. Emphasis is on methods for inducing apoptosis in cancer cells.

6 Claims, 9 Drawing Sheets

Figure 4.

(SEQ ID NO: 1)
```
1     ATGTCCACTC AACCAAAGAC ACTCACTGTT GGTCTCTTCC CATATCTTCC TTCTTGGAAT
61    GAAAATGGCA ACGAAGTTAA ATTGATCAAT TTGATCAAGG ATGTTTTGCC AACTCAGGTT
121   TCCGGATATA ATATCGAATA TACCGAATTT GATTGTTACA GTGATGCTAG TCTTCAAAGT
181   CTTCCAGATG TTTTCTCAAC TGATAGCATT TTCCTTCCAT ATCTTGTTTC TTTGGGTGGT
241   GTCAAGAGTT TGGATGAATC ATTGGTTCGT GGTGTTACTG GTGATTTGCA TAGTTTTGTT
301   TCCTCAAGTG CCTCTGTCAA TGGTTCCGTT TATGGTTTCC CACAATACTT GTGCTCAAAC
361   TTTTTATTGT CCTCACCAAA TGGTACTCAA CAAGCATCTT CCCTTTTAGA ATTGGCTCAA
421   AAGGTTGGTT ATGAACAAAT TGTTTATCCA GATGTTGCCT CTTCTAGTTC TTTCACAGTT
481   TTCGGATTGT ATCAACAATT ACTCCAATCA TCATCATCAG CTGCAGTTGA TATCAAGGCC
541   TCTGATCTTC CACAATCTGG TGACCAAGTC AACAAGGATA TCACTCAAAA ATATAGAACC
601   ATTTTGGATT CAACAGTTGT TGCCTCTCAA AGAGAATATA TTAACTCTGT AAAGCAAGGT
661   AAACCAATTT CAAACTACTA TGTCGGATAT AGTGAAAGTA TGTGTGAAAT TAAGGATATC
721   ATCAGAGATC AACAATACAA TGTTCAACTC ATTGGTACCT CTGATAAGCC ATACGTTTAT
781   ACTGATGTTT TGGCTTTGAA TTCCAATTTG TGTGATGAAA AGCAAAAGGT TGCTGTTGAA
841   GTTATCAAGA ATTTATTGAC TAATACTTTA GTTTTGGACT TGTTGGGTCT CGGATTAACT
901   CTCCCAGCCA ACAAGAATGG TATTGCTCAT TTGGCTAAAT CATCAAACTT TTATGCTCAA
961   TTGAGCCAAC AATTCGATGC CAAGGAAAGT GAAGTTAGAG TTTTGAGATG TGTTGACTTT
1021  GCTAACAAGG AAGTTAAGAA TTGTGCTGGT GTCTTGAGAC CATTCCTTCA ACATATTGCT
1081  GTTGCTACTT TGCGTTGTTT GACTGCTGAC ACTGTCGAAA AGGCTAAGAG TGGTCACCCT
1141  GGTATGCCAA TTGGTATGTC ACCAATTGCC TATGTTTTGT GGAAGTTCTT CTTCAAATCA
1201  TCTAAGGATG ATGTCAATTG GTTGAACAGA GATAGATTTG TTTTGAGTAA TGGTCACGGT
1261  TGTACATTGC TTTATGCCAT GTTGCACCTC ACTGATTGTA ACTTGAGTTT GGATGATCTC
1321  AAGAATTTCA GAAGTTTGCA TTCCAAGACT CCTGGTCACC AGAATATGG TCACACTGAA
1381  GGTGTTGATG CTACTACTGG TCCATTGGGT CAAGGTGTTT GTAATGCTAT TGGTATGGCT
1441  CTCTCTGAAG CTCACTTGGC TGCTCGTTTC AATAAGGATG ACAAAATAT CTTTGATCAC
1501  CACACCTATG TTTTCCTTGG TGATGGTTGT TTGATGGAAC GTGTTGCTAT GGAAGGTCTC
1561  TCATTTGCTG GTCACCAAAA GTTGAACAAG TTGATTGTTT CTATGATGA CAATAGTATT
1621  ACTATTGATG GTAAGACTGA ATTGACCTTT ACTCAAAATA CTCCAGAAGT CATGAGAGGT
1681  TTTGGATGGC ACGTAATTGT TGTCGACAAG GCTGATAATG ACTTGGTTGG TATTAAGGAA
1721  GCTATTTTGG AAGCTCACAC TGTTACTGAC AAGCCAATCA TGATCGTTTG TAAGACTACA
1781  ATTGGTTATT CCTCAAAGGT TCAAGGTACT GCTAAGGTTC ACGGTTCTCC ATTGGGTGCT
1841  GATGGATTGA AGAATTTGAA GGAAACTTGT GGTTTCACTG GTAATGATTT CTTCCATGTT
1901  CCAGAAATTG TCAGAAAGGA CTTTGCTACT GTCATTAATA GAAATAGTGA AAAGCTCTCT
1961  CAATGGAAGC AAGTTAAATC TGCCTATGAT ACCACTCATG CTACTGAATC CCAACTCCTC
2021  CAAAGAATGA TTAATCACGA ATTGGAAGGT GATGTTATGG AAAAGTTGCC AAAATACCTC
2081  GAACAAAAGA AGATTGCTAC CAGATCTACA TCTCAACAAG TTTTGAATGC CATCTATCCA
2141  CTCATTCCTT CTCTCGTTGG TGGTTCAGCT GACTTGACTC CATCCAACTT GACTGATGTA
2201  ACTGGATGTC AAGATTTCCA ACCAAACAAT AGAGTTGGTA GATATATCAG ATTTGGTGTC
2261  CGTGAACATG CCATGGTTGC TATTGCCAAT GGTATTCTCT ATCATGGTGT TCTTAGAACC
2321  TATGTTGGTA CATTCTTGAA CTTTGCTTCA TATGCTTTGG GTGCTATCAG ATTGAGTGCC
2381  TTGTCTGGTC TTCCAAATAT TTATGTTTTC ACTCATGACA GTATTGGTCT TGGTCAAGAT
2441  GGTCCAACTC ACCAACCTGT TGAAGTTTTA CCAATGTTGA TAGCCATTCC AAATCACATT
2501  GTTTTCAGAC CTGCTGATGG TAGAGAAACC AGTGGTGCTT ATTTGTGGGC TGTTCAATCA
2581  AAGAAGACTC CATCCTCAAT GATTCTTTCT CGTCAAGATT TGCCACAATT GACTGGTACT
2641  GATATTTCAA AGGTTGCTTT GGGTGCCTAT GTTATCCAAG GTGATGCTAC TCCTGATGTT
2701  GTCCTTGTTG GTACTGGTTC TGAAGTTTCC CTCATGGTTG AAGCTGCTGA AAAGTTGAAG
2761  GCTAACCTTA AGGTTAACGT TGTTTCCATG CCAAGTTGGG AATTGTTTGT TCGTCAATCA
2821  GAAGAATACA GGAAGACTGT CTTCCCAGAT GGTATTCCAG TTGTCAGTGC CGAAGCTTCA
2881  TCAACCTTTG GTTGGACAAG CTTTGCTCAC TATGCTGTTG GTATGACTAC TTTCGGTGCT
2941  AGTGCTGCTG CTGAAGAAGT TTACAAACTC CTCAAGATTA CCTCAGACAA TGTTGCTGAA
3001  AAGGCCACCA AATTGGTTAC CAAGTATGGT AAGCAAGCTC CAAGACTCAG CTTGTCTCTT
3061  GTTGGTGAAG AACTCTAA
```

Figure 5.

(SEQ ID NO: 2)
MSTQPKTLTVGLFPYLPSWNENGNEVKLINLIKDVLPTQVSGYNIEYTEFDCYSDASLQSLPDVFSTDSIFLPYLVSLGG
VKSLDESLVRGVTGDLHSFVSSSASVNGSVYGFPQYLCSNFLLSSPNGTQQASSLLELAQKVGYEQIVYPDVASSSSFTV
FGLYQQLLQSSSSAAVDIKASDLPQSGDQVNKDITQKYRTILDSTVVASQREYINSVKQGKPISNYYVGYSESMCEIKDI
IRDQQYNVQLIGTSDKPYVYTDVLALNSNLCDEKQKVAVEVIKNLLTNTLVLDLLGLGLTLPANKNGIAHLAKSSNFYAQ
LSQQFDAKESEVRVLRCVDFANKEVKNCAGVLRPFLQHIAVATLRCLTADTVEKAKSGHPGMPIGMSPIAYVLWKFFFKS
SKDDVNWLNRDRFVLSNGHGCTLLYAMLHLTDCNLSLDDLKNFRSLHSKTPGHPEYGHTEGVDATTGPLGQGVCNAIGMA
LSEAHLAARFNKDGQNIFDHHTYVFLGDGCLMERVAMEGLSFAGHQKLNKLIVFYDDNSITIDGKTELTFTQNTPEVMRG
FGWHVIVVDKADNDLVGIKEAILEAHTVTDKPIMIVCKTTIGYSSKVQGTAKVHGSPLGADGLKNLKETCGFTGNDFFHV
PEIVRKDFATVINRNSEKLSQWKQVKSAYDTTHATESQLLQRMINHELEGDVMEKLPKYLEQKKIATRSTSQQVLNAIYP
LIPSLVGGSADLTPSNLTDVTGCQDFQPNNRVGRYIRFGVREHAMVAIANGILYHGVLRTYVGTFLNFASYALGAIRLSA
LSGLPNIYVFTHDSIGLGQDGPTHQPVEVLPMLIAIPNHIVFRPADGRETSGAYLWAVQSKKTPSSMILSRQDLPQLTGT
DISKVALGAYVIQGDATPDVVLVGTGSEVSLMVEAAEKLKANLKVNVVSMPSWELFVRQSEEYRKTVFPDGIPVVSAEAS
STFGWTSFAHYAVGMTTFGASAAAEEVYKLLKITSDNVAEKATKLVTKYGKQAPRLSLSLVGEEL

Figure 6.

(SEQ ID NO: 3)

ATGTCCACTCAACCAAAGACACTCACTGTTGGTCTCTTCCCATATCTTCCTTCTTGGAATGAAAATGGCAACGAAGTTAA

ATTGATCAATTTGATCAAGGATGTTTTGCCAACTCAGGTTTCCGGATATAATATCGAATATACCGAATTTGATTGTTACA

GTGATGCTAGTCTTCAAAGTCTTCCAGATGTTTTCTCAACTGATAGCATTTTCCTTCCATATCTTGTTTCTTTGGGTGGT

GTCAAGAGTTTGGATGAATCATTGGTTCGTGGTGTTACTGGTGATTTGCATAGTTTTGTTTCCTCAAGTGCCTCTGTCAA

TGGTTCCGTTTATGGTTTCCCACAATACTTGTGCTCAAACTTTTTATTGTCCTCACCAAATGGTACTCAACAAGCATCTT

CCCTTTTAGAATTGGCTCAAAAGGTTGGTTATGAACAAATTGTTTATCCAGATGTTGCCTCTTCTAGTTCTTTCACAGTT

TTCGGATTGTATCAACAATTACTCCAATCATCATCATCAGCTGCAGTTGATATCAAGGCCTCTGATCTTCCACAATCTGG

TGACCAAGTCAACAAGGATATCACTCAAAAATATAGAACCATTTTGGATTCAACAGTTGTTGCCTCTCAAAGAGAATATA

TTAACTCTGTAAAGCAAGGTAAACCAATTTCAAACTACTATGTCGGATATAGTGAAAGTATGTGTGAAATTAAGGATATC

ATCAGAGATCAACAATACAATGTTCAACTCATTGGTACCTCTGATAAGCCATACGTTTATACTGATGTTTTGGCTTTGAA

TTCCAATTTGTGTGATGAAAAGCAAAAGGTTGCTGTTGAAGTTATCAAGAATTTATTGACTAATACTTTAGTTTTGGACT

TGTTGGGTCTCGGATTAACTCTCCCAGCCAACAAGAATGGTATTGCTCATTTGGCTAAATCATCAAACTTTTATGCTCAA

TTGAGCCAACAATTCGATGCCAAGGAAAGTGAAGTTAGAGTTTTGAGATGTGTTGACTTTGCTAACAAGGAAGTTAAGAA

TTGTGCTGGTGTCTTGAGACCATTCCTT

Figure 7. (SEQ ID NO: 3/SEQ ID NO: 4)

```
1/1                                     31/11
ATG TCC ACT CAA CCA AAG ACA CTC ACT GTT GGT CTC TTC CCA TAT CTT CCT TCT TGG AAT
Met ser thr gln pro lys thr leu thr val gly leu phe pro tyr leu pro ser trp asn 61/21                                   91/31
GAA AAT GGC AAC GAA GTT AAA TTG ATC AAT TTG ATC AAG GAT GTT TTG CCA ACT CAG GTT
glu asn gly asn glu val lys leu ile asn leu ile lys asp val leu pro thr gln val 121/41                                  151/51
TCC GGA TAT AAT ATC GAA TAT ACC GAA TTT GAT TGT TAC AGT GAT GCT AGT CTT CAA AGT
ser gly tyr asn ile glu tyr thr glu phe asp cys tyr ser asp ala ser leu gln ser 181/61                                  211/71
CTT CCA GAT GTT TTC TCA ACT GAT AGC ATT TTC CTT CCA TAT CTT GTT TCT TTG GGT GGT
leu pro asp val phe ser thr asp ser ile phe leu pro tyr leu val ser leu gly gly 241/81                                  271/91
GTC AAG AGT TTG GAT GAA TCA TTG GTT CGT GGT GTT ACT GGT GAT TTG CAT AGT TTT GTT
val lys ser leu asp glu ser leu val arg gly val thr gly asp leu his ser phe val 301/101                                 331/111
TCC TCA AGT GCC TCT GTC AAT GGT TCC GTT TAT GGT TTC CCA CAA TAC TTG TGC TCA AAC
ser ser ser ala ser val asn gly ser val tyr gly phe pro gln tyr leu cys ser asn 361/121                                 391/131
TTT TTA TTG TCC TCA CCA AAT GGT ACT CAA CAA GCA TCT TCC CTT TTA GAA TTG GCT CAA
phe leu leu ser ser pro asn gly thr gln gln ala ser ser leu leu glu leu ala gln 421/141                                 451/151
AAG GTT GGT TAT GAA CAA ATT GTT TAT CCA GAT GTT GCC TCT TCT AGT TCT TTC ACA GTT
lys val gly tyr glu gln ile val tyr pro asp val ala ser ser ser ser phe thr val 481/161                                 511/171
TTC GGA TTG TAT CAA CAA TTA CTC CAA TCA TCA TCA TCA GCT GCA GTT GAT ATC AAG GCC
phe gly leu tyr gln gln leu leu gln ser ser ser ser ala ala val asp ile lys ala 541/181                                 571/191
TCT GAT CTT CCA CAA TCT GGT GAC CAA GTC AAC AAG GAT ATC ACT CAA AAA TAT AGA ACC
ser asp leu pro gln ser gly asp gln val asn lys asp ile thr gln lys tyr arg thr 601/201                                 631/211
ATT TTG GAT TCA ACA GTT GTT GCC TCT CAA AGA GAA TAT ATT AAC TCT GTA AAG CAA GGT
ile leu asp ser thr val val ala ser gln arg glu tyr ile asn ser val lys gln gly 661/221                                 691/231
AAA CCA ATT TCA AAC TAC TAT GTC GGA TAT AGT GAA AGT ATG TGT GAA ATT AAG GAT ATC
lys pro ile ser asn tyr tyr val gly tyr ser glu ser met cys glu ile lys asp ile 721/241                                 751/251
ATC AGA GAT CAA CAA TAC AAT GTT CAA CTC ATT GGT ACC TCT GAT AAG CCA TAC GTT TAT
ile arg asp gln gln tyr asn val gln leu ile gly thr ser asp lys pro tyr val tyr 781/261                                 811/271
ACT GAT GTT TTG GCT TTG AAT TCC AAT TTG TGT GAT GAA AAG CAA AAG GTT GCT GTT GAA
thr asp val leu ala leu asn ser asn leu cys asp glu lys gln lys val ala val glu 841/281                                 871/291
GTT ATC AAG AAT TTA TTG ACT AAT ACT TTA GTT TTG GAC TTG TTG GGT CTC GGA TTA ACT
val ile lys asn leu leu thr asn thr leu val leu asp leu leu gly leu gly leu thr ]

901/301                                 931/311
CTC CCA GCC AAC AAG AAT GGT ATT GCT CAT TTG GCT AAA TCA TCA AAC TTT TAT GCT CAA
leu pro ala asn lys asn gly ile ala his leu ala lys ser ser asn phe tyr ala gln 961/321                                 991/331
TTG AGC CAA CAA TTC GAT GCC AAG GAA AGT GAA GTT AGA GTT TTG AGA TGT GTT GAC TTT
leu ser gln gln phe asp ala lys glu ser glu val arg val leu arg cys val asp phe 1021/341                                1051/351
GCT AAC AAG GAA GTT AAG AAT TGT GCT GGT GTC TTG AGA CCA TTC CTT
ala asn lys glu val lys asn cys ala gly val leu arg pro phe leu
```

Figure 8-1.

| Abbrev. | Genbank | Enzyme and Organism |
|---|---|---|
| ScTKT1ct - | P23254 | Transketolase of Saccharomyces cerevisiae |
| CpTKT7ct - | Q42677 | Transketolase of Craterostigma plantagineum |
| EcTKT2ct - | P33570 | Transketolase of Escherichia coli |
| BsTKTct - | P45694 | Transketolase of Bacillus subtilis |
| MgTKT - | P47312 | Transketolase of Mycoplasma genitalium |
| MjPTK1 - | Q58092 | Transketolase of Methanococcus jannaschii |
| BSTP - | P45741 | Thiaminase I precursor from Bacillus thiaminolyticus |
| N4OKAT - | -----> | Thiaminase I of Naegleria gruberi, aa 1-356 |

```
ScTKT1ct    ADDVK---QLKSKFGFNPDKSFVVPQEVYD-HYQKTILKPGVEANNKWNKLFSEYQKKFP   56
CpTKT7ct    PKEAE---ATRKNLGW-PYEPFHVPDDVKK-HWSRHIAE-GAALESAWNAKFAEFQKKFP
EcTKT2ct    EEEVA---LARQKLGW-HHPPFEIPKEIY--HAWDAREK-GEKAQQSWNEKFAAYKKAHP
BsTKTct     KEESK---LTKEAYAWTYEEDFYVPSEVYE-HFAVAVKESGEKKEQEWNAQFAKYKEVYP
MgTKT       EVDFQ---LFEKRTNT-NFNFFNYPDSIYH-WFKQTVIERQKQIKEDYNNLLISLKDK-P
MjPTK1      ------------------------------------------------------------
BsTP        MSKVKGFIYKPLMVMLALLLVVVSPAGAGAAHSDASSDITLKVAIYPYVPDPARFQAAVL
N4OKAT      MSTQP----KTLTVGLFPYL----PS-----WNENGNEVKLINLIKDVLPT---------

ScTKT1ct    ELGAELARRLSGQLPANWESKLPTYTAKDSA----VATRKLSETVLEDVYNQLPELIGGS   112
CpTKT7ct    EEAADLKSIITGELPTNWESIFPTYTPENPG----LPTRTLSHQILNGLGDVLPGLLGGS
EcTKT2ct    QLAEEFTRRMSGGLPKDWEKTTQKYINELQANPAKIATRKASQNTLNAYGPMLPELLGGS
BsTKTct     ELAEQLELAIKGELPKDWDQEVPVYE-KGSS----LASRASSGEVLNGLAKKIPFFVGGS
MgTKT       -LFKKFTNWIDSDFQALYLNQLDEKKVAKKD----SATRNYLKDFLNQINNPNSNLYCLN
MjPTK1      -------------------MVKLSGVYKG------MRKGYGETLIELGKKYENLVVLD
BsTP        DQWQRQEPGVKLEF-TDWDSYSADPPDDLDV----FVLDSIFLSHFVDAGYLLP-FGSQD
N4OKAT      -----QVSGYNIEY-TEFDCYSDASLQSLPD---VFSTDSIFLPYLVSLGGVKSLDESLV

ScTKT1ct    ADLTPSNLTRWKEALDFQPPSSGSGNYSGRYIRYGIREHAMGA---IMNGISAFGANYKPYGG   172
CpTKT7ct    ADLTLSNMAFLKNSGDFQKKSPGE-----RNVKFGAREHAMGS---ICNGLALHSPGLLPYCA
EcTKT2ct    ADLAPSNLTIWKGSVSLKEDPAGN------YIHYGVREFGMTA---IANGIAHHG-GFVPYTA
BsTKTct     ADLAGSNKTTIKNAGDFTAVDYSG-----KNFWFGVREFAMGA---ALNGMALHG-GLRVFGG
MgTKT       ADVSRS--CFIKIGDDNLHENPCS-----RNIQIGIREFAMAT---IMNGMALHG-GIKVMGG
MjPTK1      ADLSGS-----TQTAMFAKEFPE------RFFNAGVAEQNMIG---MAAGLATTG--KIVFAS
BsTP        IDQAEDVLPFALQGAKRNGEVYGLP-------QILCTNLLFYRKGDLKIGQVDNIYELYKKIG
N4OKAT      RGVTGDLHSFVSSSASVNGSVYGFP-------QYLCSNFLLSS----PNGTQQAS-SLLELAQ
                    . : .                            . .|         *
                                                     Catalytic Cys ScTKT1ct    TFLNFVS-YAAGAVR-LSALSGHPVIWVATHDSIGV-GE----DG-PTHQPIET--LAHF   222
CpTKT7ct    TYFVFTD-YMRAAMR-ISALSKARVLYIMTHDSIGL-GE----DG-PTHQPVEH--LASF
EcTKT2ct    TFLMFVE-YARNAAR-MAALMKARQIMVYTHDSIGL-GE----DG-PTHQAVEQ--LASL
BsTKTct     TFFVFSD-YLRPAIR-LAALMGLPVTYVFTHDSIAV-GE----DG-PTHEPVEQ--LASL
MgTKT       TFLAFAD-YSKPAIR-LGALMNLPVFYVYTHDSYQV-GG----DG-PTHQPYDQ--LPML
MjPTK1      SFSMFASGRAWEIIRNLVAYPKLNVKIVATHAGITV-GE----DG-ASHQMCED--IAIM
BsTP        TSHSEQIPPPQNKGLLINMAGGTTKASMYLEALIDVTGQYTEYDLLPPLDPLNDKVIRGL
N4OKAT      KVGYEQIVYPDVASSSSFTVFGLYQQLLQSSSSAAV-------DIKASDLPQSGD-QVNK
                       .             :      *  ..       .
                            (SEQ ID NO: 12) Peptide A -> ASDLPQSGD-QVNK
```

Figure 8-2.

```
ScTKT1ct    RSLPNIQVWRPADGN-EVSAAYKNSLESKHTPSIIALSRQNLPQLEGS---SIESASKGG  278
CpTKT7ct    RAMPNILTLRPADGN-ETAGAYRAAVQNGERPSILVLARQKLPQLPGT---SIEGVSKGG
EcTKT2ct    RLTPNFSTWRPCDQV-EAAVGWKLAVERHNGPTALILSRQNLAQVERTPD-QVKEIARGG
BsTKTct     RAMPNLSLIRPADGN-ETAAAWKLAVQSTDHPTALVLTRQNLPTIDQTSEEALAGVEKGA
MgTKT       RAIENVCVFRPCDEK-ETCAGFNYGLLSQDQTTVLVLTRQPLKSIDNTD--SLKTL-KGG
MjPTK1      RAIPNMVVIAPTDYY-HTKNVIRTIAEYKG-PVYVRMPRRDTEIIYENEEEATFEIGKGK
BsTP        RLLINMAGEKPSQYVPEDGDAYVRASWFAQ-GSGRAFIGYSESMMRMG---DYAEQVRFK
N40KAT      DITQKYRTILDSTVV-ASQREYINSVKQGK-PISNYYVGYSESMCEIK---DIIRDQQYN
                              :
        Peptide B -> TILDSTVV-ASQR   (SEQ ID NO: 13)

ScTKT1ct    YVLQDVAN-----PDIILVATGSEVSLSVEAAKTLAAKNIKARVVSLPDFFTFDKQPLE-  332
CpTKT7ct    YVISDNSRGGNSKPDVILIGTGSELEIAARAGDELRKEGKKVRVVSLVCWELFAEQSEK-
EcTKT2ct    YVLKDSGG----KPDIILIATGSEMEITLQAAEKLAGEGRNVRVVSLPSTDIFDAQDEE-
BsTKTct     YVVSKSKN--E-TPDALLIASGSEVGLAIEAQAELAKENIDVSVVSMPSMDRFEKQSDE-
MgTKT       YILLDRKQ-----PDLIIAASGSEVQLAIEFEKVLTKQNVKVRILSVPNITLLLKQDEK-
MjPTK1      ILVDG--------EDLTIIATGEEVPEALRAGEILKENGISAEIVEMATIKPIDEEIIKK
BsTP        PISSSAG------QDIPLFYSDVVSVNSKTAHPELAKKLANVMASADTVEQALRPQADGQ
N40KAT      VQLIGTS-------DKPYVYTDVLALNSN---LCDEKQKVAVEVIKNLLTNTLVLDLLG-
                   *      :.       :              :         :   :

ScTKT1ct    YRLSVLPDNVPI-MSVEVLATTCWGKYAH------QSFGIDRFGASGKAPEVFKFFGFTP  385
CpTKT7ct    YRETVLPSGVTARVSVEAGSTFGWERFIGP-KG--KAVGIDRFGASAPAERLFKEFGITV
EcTKT2ct    YRESVLPSNVAARVAVEAGIADYWYKYVGL-KG--AIVGMTGYGESAPADKLFPFFGFTA
BsTKTct     YKNEVLPADVKKRLAIEMGSSFGWGKYTGL-EG--DVLGIDRFGASAPGETIINEYGFSV
MgTKT       YLKSLFDANSSL-ITIEASSSYEWFCFKKY-VKNHAHLGAFSFGESDDGDKVYQQKGFNL
MjPTK1      SKDFVVTVEDHSIIGGLGGAVAEVIASNGLNKKLLRIGINDVFGRSGKADELLKYYGLDG
BsTP        YPQYLLPARHQV-YEALMQDYPIYSELAQIVNK--PSNRVFRLGPEVRT-WLKDAKQVLP
N40KAT      -LGLTLPANKNG-IAHLAKSSNFYAQLSQ---------QFDAKESEVRVLRCVDFANKEV
                .
        Peptide C -> SSNFYAQLSQ---------QFDAK  (SEQ ID NO: 14)

ScTKT1ct    EGVAERAQKTIAFYKGDKLISPLKKAF 412   (SEQ ID NO: 5)
CpTKT7ct    EAVVA-AAKEIC---------------       (SEQ ID NO: 6)
EcTKT2ct    ENIVAKAHKVLGVKGA----------        (SEQ ID NO: 7)
BsTKTct     PNVVNRVKALINK-------------        (SEQ ID NO: 8)
MgTKT       ERLMKIFTSLRN--------------        (SEQ ID NO: 9)
MjPTK1      ESIAKRIMEEMKKE------------        (SEQ ID NO: 10)
BsTP        EALGLTDVSSLAS-------------        (SEQ ID NO: 11)
N40KAT      KNCAGVLRPFL---------------        (SEQ ID NO: 4)
```

THIAMINASES AND THIAMINASE GENES FOR USE IN APOPTOTIC THERAPIES

This application claims the benefit of Fulton et al., U.S. Provisional Application No. 60/156,952, filed Sep. 29, 1999, and is related to Fulton & Lai, U.S. patent application Ser. No. 09/113,596, filed Jul. 10, 1998, which claims the benefit of Fulton et al., U.S. Provisional Application 60/052,377, filed Jul. 11, 1997, and of Fulton et al., U.S. Provisional Application 60/087,526, filed Jun. 1, 1998, all entitled METHOD OF INDUCING APOPTOSIS BY REDUCING THE LEVEL OF THIAMIN, all of which are incorporated by reference in their entireties, including drawings.

BACKGROUND OF THE INVENTION

1. Field of the Invention

This invention is related to the field of treatment of cancer, other neoplastic disorders, and other conditions in vertebrates in which killing a specific group of cells is useful, and in particular to the use of thiamin-cleaving enzymes, thiaminases, and their expressed thiaminase genes, as a means to induce apoptotic death of targeted cells, such as cancer cells, by reducing the level of thiamin (vitamin B1) in these cells.

2. Background Information

The information provided herein is intended to aid the understanding of the reader, and is not an admission that any of the information or references is prior art to the present invention.

Most if not all cells of metazoan animals carry the machinery to commit suicide in a regular manner in response to suitable stimulus. This process is called programmed cell death, cell suicide, or apoptosis. Apoptosis is being extensively studied in mammals and other vertebrates, as well as in the worm *Caenorhabditis elegans* and the fly *Drosophila melanogaster* (reviews: Ellis et al., 1991; Steller, 1995). In vertebrate cells the process of apoptosis, which was previously termed "shrinkage necrosis," involves a regular sequence of events, including membrane blebbing, cell shrinkage, pycnosis of nuclei with margination of chromatin, and usually cleavage of DNA into nucleosome-sized fragments (Wyllie et al., 1980).

Apoptosis is an essential part of embryonic development and of the maintenance of an adult animal. In mammals, for example, during development apoptosis plays a major role in the development of the nervous system (more than 50% of the neural cells that arise during embryogenesis undergo apoptosis), in the elimination of lymphocytes that produce antibodies which recognize self, in "carving" features such as the digits of the hand, and so forth. Throughout life, orderly apoptosis is used to eliminate damaged or unwanted cells without inducing an inflammatory reaction. Blood cells, cells of the immune system, and cells of most if not all tissues normally are eliminated by the apoptotic mechanism.

Failures of apoptosis produce or contribute to severe diseases, including autoimmune diseases and some cancers. It has been argued that one of the major causes of the development and progression of many cancers is a reduction of the occurrence of apoptosis (Wylie, 1985; Fisher, 1994; Hickman et al., 1994; Martin and Green, 1995; Thompson, 1995).

A wide variety of signals induce apoptosis in suitable target cells (Gerschenson and Rothello, 1992; Thompson, 1995). Radiation and many valuable chemotherapeutic agents, such as cisplatin and other platinum compounds, induce apoptosis (e.g., Eastman, 1990; Hickman, 1992; Chu, 1994a). These agents affect many cell types. Specialized cell types are dependent on specific growth factors (e.g., nerve growth factor for certain neuronal cells, interleukin-2 for certain lymphocytes) and undergo apoptosis if the required factors are unavailable. Other cell types have receptors for specific agents that can induce apoptosis in these cell types (e.g., glucocorticoid for thymocytes, tumor necrosis factor in suitable target cells) (e.g., Rubin et al., 1988).

The mechanism of apoptosis is just beginning to be understood. Some have suggested that all cells are poised to die, and that they are kept alive by constant "survival signals" that keep the suicide machinery inactive (Raff, 1992). It is clear that many if not all vertebrate cells contain preformed machinery for apoptosis, since there are many examples of cells that undergo apoptosis even without synthesis of new proteins (Waring, 1990). There also are cases in which protein synthesis is required (reviewed by Cohen, 1993).

Several elements that appear to be part of the apoptotic machinery have been identified and are receiving much attention. Two that should be mentioned are bcl-2 and its family members and p53. Exactly how these are related to the apoptotic machinery is still being defined.

Expression of oncogene bcl-2 in cells markedly delays or blocks induction of apoptosis by many agents, including some that are valuable in chemotherapy of tumors, such as cisplatin (Reed, 1994; Korsmeyer, 1995; Thompson, 1995). There are a few cases in which induction of apoptosis is unaffected by expression of bcl-2 (e.g., Sentman et al., 1991; Vaux et al., 1992). High-level expression of bcl-2 is common in tumors, including breast carcinomas, small cell lung cancer, androgen-independent prostate cancer, and neuroblastoma (Hickman et al., 1994). In some cases expression of bcl-2 is correlated with a poor prognosis for therapy (Reed, 1994).

Functional tumor suppressor gene product p53 is required for induction of cell death by irradiation and many chemotherapeutic agents (Lowe et al., 1993), as well as by oxygen deficiency at the center of solid tumors (Graeber et al., 1996). On the other hand, the normal development of transgenic animals nullizygous for the p53 gene indicates that p53 is not required for the extensive apoptosis that occurs during development (Donehower et al., 1992). Other cases of p53-independent apoptosis have been described (White, 1993; Zhuang et al., 1995). Many established lines of cells in culture have lost p53 function. In tumors in vivo, loss of p53 function is common, and this loss is correlated with tumor aggressiveness and indicates a poor prognosis for treatment by standard protocols of chemotherapy and radiation (Fisher, 1994; Hartmann et al., 1997).

As an example, the roles of p53 loss and bcl-2 expression in the development and progression of colon carcinomas have been described and analyzed (Hickman et al., 1994; Sinicrope et al., 1996).

A previous patent application (Pat1) described methods for inducing apoptosis of a selected group of cells in vivo by reducing the level of thiamin in these cells. Methods for inducing apoptosis of cancer cells were included. Compounds and compositions for use as methods of thiamin depletion and treating disease such as cancer were also described.

SUMMARY OF THE INVENTION

The present invention is based on our discovery that apoptotic cell death can be induced in diverse cell types by creating a deficiency in the natural vitamin, thiamin and brings together three disparate areas: a) the programmed death or apoptosis of vertebrate cells, b) an agent in the unicellular protist *Naegleria* and in certain other organisms that induces delayed apoptosis, even in quiescent cells, and c) thiamin deficiency.

The invention provides a method for inducing death in selected cells in vivo by using localized delivery of thiamin-depleting compounds to reduce the thiamin in these cells below a critical level. This method, localized apoptosis induced by depletion of thiamin (LAIDT), is applicable to therapy of cancer and to elimination of other targetable cells. Furthermore, the method allows rapid and convenient reversal of the effects of the deficiency at any time such reversal is desired, simply by the administration of replacement thiamin.

This method allows the selective killing of a group of cells, for example a tumor mass, by localizing the deficiency of thiamin to the desired cell group. Both the thiamin depletion and the targeting can be accomplished in a variety of different ways, as described in Fulton et al., U.S. patent application Ser. No. 09/113,596, filed Jul. 10, 1998, and International application No. PCT/US98/14496, both entitled METHOD OF INDUCING APOPTOSIS BY REDUCING THE LEVEL OF THIAMIN. Typically however, the method involves the delivery of a thiamin-depleting agent or a nucleic acid sequence encoding a thiamin-depleting agent to the desired cell group. The creation of the thiamin deficiency, which results from the delivery of the thiamin-depleting agent, leads to programmed cell death, or apoptosis. This method is broadly applicable to use with cells of vertebrate organisms, which cannot produce their own thiamin and so rely on exogenously provided, i.e., dietary, thiamin to provide the cellular requirements. In particular, the method can be utilized in vivo in a vertebrate organism, for example a human.

This invention utilizes a novel paradigm for cancer therapy, in addition to those currently commonly used or tested (e.g., radiation, chemotherapy, immunotherapy, gene therapy, and antiangiogenesis therapy). In this paradigm, selective starvation of cancer cells for a particular required nutrient whose absence induces apoptosis, in this description the essential vitamin, thiamin, leads to death of the cancer cells.

Thus in a first aspect, the invention provides a method for inducing apoptosis of a selected group of vertebrate cells in vivo by sufficiently reducing the level of thiamin in cells of the group, by administering a thiaminase or a thiaminase derivative. For example, the cells may be neoplastic cells, e.g., cancer cells.

Preferably the thiaminase is a eukaryotic thiaminase or a Type 2 thiaminase, or derivative thereof. In particular embodiments, the thiaminase is a *Naegleria gruberi* thiaminase or a *Bacillus thiaminolyticus* thiaminase, or a *Clostridium sporogenes* thiaminase, or derivative thereof.

Although emphasis herein is on use of LAIDT for cancer therapy, thiamin deficiency and the methodology herein allows therapeutic elimination of other unwanted cells.

Thiaminases are described in detail in Fulton et al., U.S. patent application Ser. No. 09/113,596, and PCT/US98/14496, and are a preferred embodiment for LAIDT along with derivatives of thiaminases. Most organisms do not appear to have any thiaminase activity. There are two types, thiaminase I that cleaves thiamin by a base-substitution reaction and the rarer thiaminase II that cleaves thiamin by direct hydrolysis (reviewed by (Evans, 1975; Fujita, 1954)). None has been found in mammals or birds (e.g., Harris, 1951; Puzach, 1991). Thiaminase I has been found in some but not all shellfish, some fresh-water fish (especially of the carp family), a few plants (especially ferns such as bracken), one protozoan (*Naegleria gruberi*), and scattered bacteria (including *Bacillus thiaminolyticus* and *Clostridium sporogenes*). Prior to this invention, only the thiaminase I of *Bacillus thiaminolyticus* has been cloned ((Abe et al., 1987)) or sequenced ((Costello et al., 1996)) (DNA sequence no. U17168).

In another aspect, the invention provides a pharmaceutical composition containing a nucleic acid molecule encoding a thiaminase or a thiaminase derivative and a pharmaceutically acceptable carrier or excipient.

In another aspect, the invention provides an isolated, purified, or enriched nucleic acid molecule encoding a non-*Bacillus thiaminolyticus* thiaminase, or a derivative (including a fragment) of such a thiaminase with thiamin-cleaving and/or thiamin-binding activity. Preferably the thiaminase or derivative is a *Naegleria gruberi* thiaminase or derivative:

In preferred embodiments, the nucleic acid molecule encodes a thiaminase or thiaminase derivative homologous to a *Naegleria gruberi* thiaminase.

By "homologous" is meant that a particular sequence from a thiaminase or thiaminase gene had at least 70% sequence identify, as defined by a maximal base match in a computer-generated alignment, at the nucleotide level with the reference sequence, preferably at least 80%, and more preferably at least 85%, over at least a 50 nucleotide window, preferably over at least a 75 or 100 nucleotide window, more preferably over at least a 200, 300, 400, or 500 nucleotide window, and most preferably over the entire coding sequence or over the entire gene. Likewise, homology can be shown by at least 25% sequence identity at the polypeptide level as compared to a reference sequence, preferably at least 35%, 40%, 45%, 50%, 55%, 60%, 70%, or even more, or by sequence similarity of at least 45%, preferably at least 50%, 60%, 70%, 80%, or even more.

For nucleotide or amino acid sequence comparisons where a homology is defined by a % sequence identity, the percentage is determined using BLAST programs (with default parameters (Altschul et al., 1997, "Gapped BLAST and PSI-BLAST: a new generation of protein database search programs, Nucleic Acid Res. 25:3389-3402)). Any of a variety of algorithms known in the art that provide comparable results can also be used, preferably using default parameters. Performance characteristics for three different algorithms in homology searching is described in Salamov et al., 1999, "Combining sensitive database searches with multiple intermediates to detect distant homologues." *Protein Eng.* 12:95-100. Another exemplary program package is the GCG™ package from the University of Wisconsin.

In preferred embodiment, the thiaminase is from a fern or other pteridophyte, such as the fern bracken (*Pteridium aquilinum*) or the fern nardoo (*Marsilea drummondii*). In still another, the thiaminase is from a fish, preferably of the family Cyprinidae, such as carp.

In the case of nucleic acid sequences encoding thiaminase derivatives, it is often advantageous for the encoded amino acid sequence to be shorter than a full length naturally occurring thiaminase. Therefore, in preferred embodiments, the nucleic acid sequence encodes a modified thiaminase or thiaminase derivative containing about 90% or less, 80% or less, 70% or less, 60% or less, 50% or less, or 40% or less or the amino acid sequence of the corresponding natural thiaminase. Thus, for example, the nucleic acid sequence can encode a derivative having about 400 or fewer, 200 or fewer, 100 or fewer, or 50 or fewer amino acids. Similarly, the nucleic acid sequence can encode a polypeptide thiamin-binding compound or derivative.

By "isolated" in reference to nucleic acid is meant a polymer of nucleotides conjugated to each other, including DNA or RNA that is isolated from a natural source or that is synthesized. The isolated or synthesized (e.g., cDNA) nucleic acids of the present invention are unique in the sense that they are not found in a pure or separated state in nature. Use of the term "isolated" indicates that a naturally occurring sequence has been removed from its normal cellular (i.e., chromosomal) environment. Thus, the sequence may be in a cell-free solution or placed in a different cellular environment. The term does not imply that the sequence is the only nucleotide sequence present, but that it is essentially free (about 90-95% pure at least) of non-nucleotide material naturally associated with it and thus is meant to be distinguished from isolated chromosomes.

By the use of the term "enriched" in reference to nucleic acid is meant that the specific DNA or RNA sequence constitutes a significantly higher fraction (2-5 fold greater, more preferably >100-fold) of the total DNA or RNA present in the cells or solution of interest than in normal or diseased cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased. The term "significant" here is used to indicate that the level of increase is useful to the person making such an increase, and generally means an increase relative to other nucleic acids of about at least 2 fold, more preferably at least 5- to 10-fold, more preferably at least 100- to 1000-fold, or even more. The term also does not imply that there is no DNA or RNA from other sources. The other source DNA may, for example, comprise DNA from a yeast or bacterial genome, or a cloning vector. This term distinguishes the sequence from naturally occurring enrichment events, such as viral infection, or tumor type growths, in which the level of one mRNA may be naturally increased relative to other species of mRNA. That is, the term is meant to cover only those situations in which a person has intervened to elevate the proportion of the desired nucleic acid.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level this level should be at least 2-5 fold greater, e.g., in terms of mg/ml, more preferably at least 100- or 1000-fold greater). Individual clones isolated from a cDNA or genomic library may be purified to electrophoretic homogeneity. The claimed DNA molecules obtained from these clones can be obtained directly from total DNA or from total RNA. The cDNA clones or genomic are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message. Thus, purification of at least three orders of magnitude, and more preferably four or five orders of magnitude is expressly contemplated. The term is also chosen to distinguish clones already in existence which may encode a thiaminase or portion of a thiaminase but which have not been isolated from other clones in a library of clones. Thus, the term covers clones encoding a thiaminase or portion of a thiaminase which are isolated from other non-thiaminase clones.

A polypeptide thiaminase can be encoded by a full-length nucleic acid sequence or portion of the full-length nucleic acid sequence. In preferred embodiments the isolated nucleic acid comprises, consists essentially of, or consists of a nucleic acid sequence encoding a naturally-occurring thiaminase, a nucleic acid sequence that hybridizes to such a nucleic acid sequence, or a functional derivative of either. The nucleic acid may be isolated from a natural source by cDNA cloning, use of PCR primers, subtractive hybridization, or other means standard to the art; the natural source may be any organism which naturally produces a thiaminase, specifically including those described in the Detailed Description below, and the nucleic acid may be synthesized by the triester or other method or by using an automated DNA synthesizer.

The term "hybridize" refers to a method of interacting a nucleic acid sequence with a DNA or RNA molecule in solution or on a solid support, such as . . . cellulose or nitrocellulose. If a nucleic acid sequence binds to the DNA or RNA molecule with high affinity, it is said to "hybridize" to the DNA or RNA molecule. The strength of the interaction between the probing sequence and its target can be assessed by varying the stringency of the hybridization conditions. Various low or high stringency hybridization conditions may be used depending upon the specificity and selectivity desired. Stringency is controlled by varying salt or denaturant concentrations. Examples of hybridization conditions are shown in the examples below. Those skilled in the art will recognize how such conditions can be varied to vary specificity and selectivity. Under highly stringent hybridization conditions only highly complementary nucleic acid sequences hybridize. Preferably, such conditions prevent hybridization of nucleic acids having one or two mismatches out of 20 contiguous nucleotides.

The invention also features recombinant nucleic acid encoding a thiaminase or thiaminase derivative, preferably in a vector effective to initiate transcription in a host cell. The vector may be in such a eukaryotic host cell or in vivo in cells of an organism. The recombinant nucleic acid can, for example, contain a transcriptional initiation region functional in a cell, a sequence complementary to an RNA sequence encoding a thiamin-depleting agent polypeptide and a transcriptional termination region functional in a cell. While recombinant nucleic acid encoding an unmodified thiaminase, for example in a eukaryotic expression vector, from *Bacillus thiaminolyticus* can be utilized in the methods of this invention, in certain embodiments the encoded thiaminase agent is different from that enzyme, e.g., a eukaryotic thiaminase and in other embodiments is not a modification or derivative of that thiaminase.

Thus, in a related aspect the invention provides a eukaryotic expression vector which includes a nucleic acid sequence encoding a thiaminase or thiaminase derivative. The expression vector is constructed and adapted for expression in eukaryotic cells, preferably in human cells. Preferably the vector does not include an origin of replication functional in eukaryotic cells. While vectors based on viral sequences can be beneficially used, in preferred embodiments, the vector is a non-viral vector, meaning that the vector does not contain sufficient viral sequences to cause viral replication or capsid formation. In certain embodiments, the encoded thiamin-depleting agent differs from a full-length thiaminase from *Bacillus thiaminolyticus* and in other embodiments is not a modification or derivative or that thiaminase. Other preferred embodiments are as described above for the nucleic acids and nucleic acid delivery methods.

In another related aspect, the invention provides a vector which includes a recombinant nucleic acid sequence which encodes a polypeptide thiaminase or a thiaminase derivative which is different from a *Bacillus thiaminolyticus* thiaminase. In preferred embodiments, the vector is an expression vector which is constructed and adapted for expression in prokaryotic cells, for example, *E. coli*, though a variety of other bacteria can be used. In other embodiments the vector is a eukaryotic expression vector, which is constructed and adapted for expression in eukaryotic cells. Other preferred embodiments are as described for the vectors, nucleic acids and nucleic acid delivery methods above.

In accord with the vectors and methods for delivery of nucleic acid encoding a thiaminase, the invention also provides a eukaryotic cell transfected with a eukaryotic expression vector containing a nucleic acid sequence encoding a thiaminase. Preferably, the cell is a vertebrate cell in vivo in a vertebrate organism, such as a bird or a mammal, e.g., a human. The thiaminase can be any peptide or polypeptide compound, such as those described in the above aspects.

In another related aspect, the invention provides a composition for delivery of a nucleic acid sequence encoding a thiaminase or a thiaminase derivative to vertebrate cells in vivo. The composition includes a nucleic acid sequence encoding the thiaminase or a thiaminase derivative. The composition preferably also includes a component associated with a nucleic acid sequence which enhances delivery of the nucleic acid into the cells. In preferred embodiments, the nucleic acid and other components of the composition are as described above in connection with methods involving delivery of a nucleic acid sequence.

Thiaminases and derivatives obtained from natural sources will be useful as described for the methods of this invention, and for analysis for constructing derivatives and synthetic thiamin-cleaving compounds. Thus, another aspect of the invention features an isolated, enriched, or purified polypeptide thiaminase which has not previously been obtained. In the case of an agent which has been enriched or partially purified, the invention provides a purified agent, so that the agent is separated from at least 95%, preferably from at least 98%, and still more preferably from at least 99% of the macromolecules from the environment in which the agent is naturally produced. The agent therefore differs from a *Bacillus thiaminolyticus* thiaminase or mutated form of that thiaminase involving substitution or deletion of less than 1%, 5%, or 10% of the amino acid sequence of that thiaminase. In preferred embodiments, the agent is a thiaminase or thiaminase derivative.

The invention also provides an isolated, purified, or enriched nucleic acid molecule that has a nucleotide sequence at least 90% identical, preferably at least 95%, 97%, 98%, 99%, or 100% to a portion of a *Naegleria gruberi* thiaminase gene or coding sequence at least 15, 17, 20, 25, 30, 35, 40, 50, 75, 100, 200, or even more nucleotides in length.

In another aspect, the invention provides an isolated, purified, or enriched non-Bacillus thiaminolyticule thiaminase polypeptide, or a derivative thereof having thiamin-cleaving and/or thiamin-binding activity.

By "isolated" in reference to a polypeptide is meant a polymer of 6, 12, 18 or more amino acids conjugated to each other, including polypeptides that are isolated from a natural source or that are synthesized. In this invention, the polypeptide will commonly have at least about 50, 100, 200, or 400 amino acids conjugated together. The isolated polypeptides of the present invention are unique in the sense that they are not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only amino acid chain present, but that it is essentially free (about 90-95% pure at least) of material naturally associated with it.

By the use of the term "enriched" in reference to a polypeptide it is meant that the specific amino acid sequence constitutes a significantly higher fraction (2- to 5-fold greater) of the total of polypeptide present in the cells or solution of interest than in normal or diseased cells or in the cells from which the sequence was taken. This could be caused by a person by preferential reduction in the amount of other polypeptides present, or by a preferential increase in the amount of the specific amino acid sequence of interest, or by a combination of the two. However, it should be noted that "enriched" does not imply that there are no other amino acid sequences present, just that the relative amount of the sequence of interest has been significantly increased. The term significant here is used to indicate that the level of increase is useful to the person making such an increase, and generally means an increase relative to other polypeptides of about at least 2-fold, more preferably at least 5 to 10 fold or even more. The term also does not imply that there is no polypeptide from other sources. The other source polypeptide may, for example, comprise amino acid encoded by a yeast or bacterial genome, or a cloning vector. The term is meant to cover only those situations in which a person has intervened to elevate the proportion of the desired polypeptide.

It is also advantageous for some purposes that an amino acid sequence be in purified form. The term "purified" in reference to a polypeptide does not require absolute purity (such as a homogeneous preparation); instead, it represents an indication that the sequence is relatively purer than in the natural environment (compared to the natural level this level should be at least 2-5 fold greater, e.g., in terms of mg/ml). Purification of at least one order of magnitude, preferably two or three orders, and more preferably four or five orders of magnitude is expressly contemplated. The substance is preferably free of contamination at a functionally significant level, for example 90%, 95%, or 99% pure.

In another aspect, the invention provides a method for identifying a nucleic acid sequence coding for a thiaminase by probing for sequences which hybridize with a nucleic acid probe that contains a sequence which is the same as a sequence from a thiaminase-endoding gene of *Naegleria gruberi* or *Bacillus thiaminolyticus*. Preferably the probe contains a nucleic acid sequence at least 10 nucleotides in length with the same base sequence as the equal length sequence from the specified organism and/or a degenerate sequence that contains alternate codon usage at one or more of the codons. In preferred embodiments, the probe contains a longer sequence corresponding (the same or utilizing alternate codon usage) to the *Naegleria gruberi* or *Bacillus thiaminolyticus* thiaminase sequences or derivatives, for example, at least 12, 13, 15, 17, 20, 25, 30, 40, 50, or even more nucleotides. Preferable a plurality of probes is used that may all correspond to the same *Naegleria gruberil* or *Bacillus thiaminolyticus* sequence or may correspond to more than one such sequence or both. The probe or probes is used to hybridize to a complementary target sequence in nucleic acid from a different organism which is being tested for the presence of a thiaminase-encoding sequence, thereby identifying such a sequence if present. The target sequence need not be perfectly complementary; useful hybridization results can be provided, for example, by hybridization of complementary sequences that have 7 out of 10, 8 out of 10, 9 out of 10, or 10 out of 10 base pairing over the target sequence. The target sequence is generally in a cDNA or genomic DNA clone library, and hybridization identifies a clone insert containing the target sequence. As recognized by those skilled in the art, hybridizing clones can be sequenced and expressed using standard materials and methods to identify a coding sequence and product. If needed, additional libraries or sub-libraries can be constructed by conventional methods to identify larger or preferably full-length coding sequences.

Alternatively, for organisms for which sequence information is available, instead of probing with degenerate probe sets, sequence comparison can be used using any of the publicly available computer-based software for polynucleotide or polypeptide sequence comparisons to identify sequences which have levels of sequence similarity indicative of thiaminase function. Those accustomed to performing sequence analyses are familiar with identifying such indication of common function at either the nucleotide level or peptide level, or both, including accounting for conservative amino acid changes. Such methods can be utilized in the present method. The computer-based sequence comparisons can be used to design complementary probes that can be used to isolate the actual coding and complete gene sequences.

Additional aspects and embodiments concerning thiaminases and thiaminase derivatives, and descriptions of the preparation and use of the same are provided in the related applications identified above, and are included within the scope of the present invention.

As used in the claims to describe the various inventive aspects and embodiments, "comprising" means including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Additional features and embodiments of the present invention will be apparent from the following Detailed Description and from the claims, all within the scope of the present invention.

BRIEF DESCRIPTION OF THE TABLES

Table 1 summarizes the strategy for purifying a thiaminase, using *Naegleria* thiaminase as an example.

Table 2 presents a sample of the evidence that *Naegleria* thiaminase expressed in *E. coli* induces apoptosis, and that its ability to induce apoptosis depends on the thiaminase activity rather than any other feature of the protein.

BRIEF DESCRIPTION OF THE DRAWINGS

FIG. 4 shows the 3414 base sequence of the coding region of *Naegleria* gene TTK(SEQ ID NO: 1); the first segment of this gene (underlined) encodes thiaminase I.

FIG. 5 shows the amino acid sequence encoded by *Naegleria* gene TTK(SEQ ID NO: 2).

FIG. 6 shows the DNA sequence of the 1068 base segment that encodes the *Naegleria* thiaminase I(SEQ ID NO: 3), as obtained from *Naegleria* gene TTK. This segment, expressed as pNB1+, encodes catalytically active thiaminase.

FIG. 7 shows the 356 amino acid sequence encoded by the *Naegleria* gene segment expressed in pNB1+, along with the DNA codons(SEQ ID NOS 3 and 4).

FIG. 8 is an alignment comparing the amino acid sequence of *Naegleria* thiaminase Ito other homologous sequences, specifically the thiaminase I of *Bacillus* thiaminase I and segments of several transketolases, which we found show limited homology to the encoded sequences of the two sequenced thiaminase I proteins(SEQ ID NOS 5-11, 4 and 12-14, respectively, as they occur).

DETAILED DESCRIPTION OF THE PREFERRED EMBODIMENTS

Figure 1:
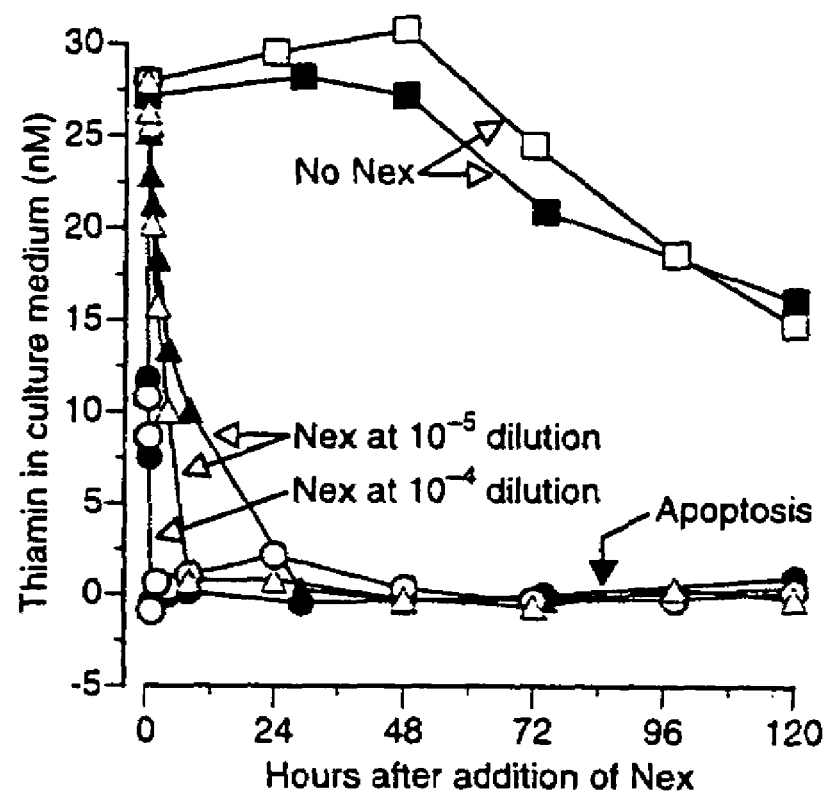
FIG. 1 is a graph showing that the *Naegleria* agent (Nex) depletes thiamin from the growth medium. Rat glioma C6 cells were grown in Medium 199 with 10% fetal bovine serum. The amount of thiamin in the medium was measured using the thiochrome method ((Wyatt et al., 1989)), in two independent experiments (open symbols and filled symbols) with cultures treated with the *Naegleria* agent at dilutions of $1 \square 10^{-4}$ and $1 \square 10^{-5}$.

As indicated above, the present invention is related to the use of thiaminases as clinically useful reagents to induce apoptotic death of cells, including but not restricted to human tumor cells. It is based on the properties of an agent from the unicellular eukaryote *Naegleria gruberi* that induces delayed apoptotic death of mammalian cells, including tumor cells. These properties are summarized below, and more fully in the related Fulton et al. applications, supra, and in Lai et al. (paper in preparation).

Many chemotherapeutic and genotoxic agents, including radiation, that are currently used in cancer therapy share several unfavorable characteristics. Besides their considerable toxicity, these agents induce apoptotic death primarily in proliferating cells, leaving the temporarily quiescent cells found in solid tumors to re-grow. The ability to induce apoptosis in quiescent cells is of great therapeutic interest, since 1) in solid tumors many cells are quiescent, 2) commonly used chemotherapeutic agents mainly kill proliferating cells, and 3) most agents that induce apoptosis in quiescent cells are too toxic to use therapeutically ((Berges et al., 1995)). In addition, the ability of many commonly used agents to induce apoptosis depends on the expression of the p53 tumor suppressor gene and is inhibited by expression of the bcl-2 oncogene, yet many tumor cells survive because they are unable to produce functional p53 protein or they overexpress bcl-2. The *Naegleria* agent, unlike common chemotherapeutic poisons, is not immediately cytotoxic but can induce apoptosis in quiescent, p53 null, and bcl-2-expressing cells. The exceptional conditions under which this agent induces apoptosis suggest new opportunities for targeted cancer therapy.

The induction of apoptosis by the *Naegleria* agent is unusual in that the agent initially has little effect on the proliferation of the cells, and induces apoptosis only after a latent period of several days. With rat glioma C6 cells the time from Nex addition to death, the latent period, is about 4 days. The agent kills diverse mammalian cells, including primary cells and established cell lines of both normal and cancer cells. As the *Naegleria* agent is serially diluted a sharp endpoint is reached after which cell death is no longer induced. The agent is very active; a $10^{-6}$ dilution that contains. 0.1 μg/1 of total *Naegleria* cell protein is sufficient to induce cell death. At the end of the latent period, death is rapid and extensive; within three days after morphological death of C6 cells ≦0.00006% clonogenic survivors remain. The agent must be present in the culture until close to the time of morphological death. If the agent is removed and rinsed away even 12 hours prior to the end of the latent period, the cells remain healthy, as if never treated. The mode of cell death is apoptosis by all tested criteria, including membrane bubbling, margination of chromatin, cleavage of nuclear DNA to oligonucleosomal fragments, externalization of phosphatidylserine, and production of apoptotic bodies.

The *Naegleria* agent can induce apoptosis in nonproliferating cells, even if the agent is added after the cells have reached stationary phase; under appropriate conditions we have demonstrated that cells can die without re-entering the S phase (DNA synthesis) of the cell cycle. The agent can also induce apoptosis in the absence of protein synthesis, indicating that it action activates the constitutive cell suicide machinery without requiring the translation of new proteins. The ability of the agent to kill is not affected by overexpression of the anti-apoptosis oncogene bcl-2. Finally, the agent is similarly effective in killing cells that express wild-type p53 or cells unable to express p53. These features offer great potential advantages for cancer therapy.

Figure 2:
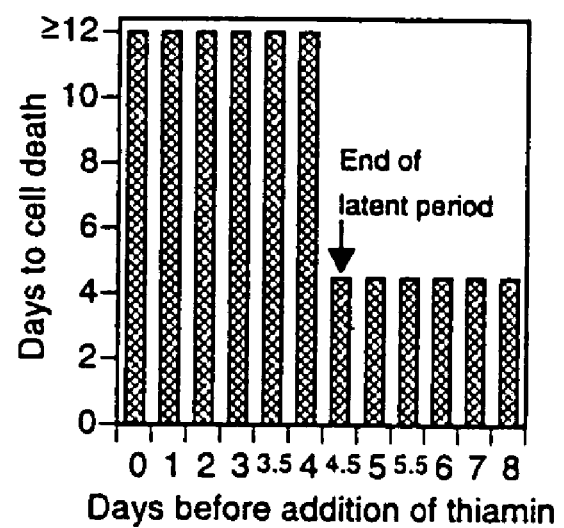
FIG. 2 shows that addition of thiamin can reverse progress toward apoptosis. Cells were plated with $2 \square 10^{-5}$ Nex. Thiamin, at 3 µM, was added to cultures at 12-24 hour intervals. In this experiment the latent period was 4.5 days.

The agent acts by depleting thiamin (vitamin B1) from the medium and thus creates a thiamin deficiency, specifically by acting as a thiaminase (Fulton et al. supra). The rapid depletion of thiamin from the medium by the *Naegleria* agent is shown in FIG. 1. At a $10^{-4}$ dilution, thiamin was unmeasurable within 4 hours. The addition of excess thiamin to cell cultures treated with the *Naegleria* agent at any time prior to the first signs of morphological death can prevent the induction of apoptosis (FIG. 2). Adding thiamin is equivalent to replacing the agent-treated growth medium with fresh medium to reverse the effect of treatment. The addition of thiamin acts as an "antidote" for the apoptosis-inducing activity of the *Naegleria* agent. This ability to reverse the effect of the agent is an unusual and powerful asset to therapeutic use. If, unexpectedly, targeted therapy using thiaminase got out of control (e.g., if unacceptable physical effects were observed), an antidote would always be available in case untargeted cells were affected at an unacceptable level or an excessive overall thiamin deficiency was created in the patient.

Any regime of drug administration, especially those involving conventional chemotherapies, includes the possibilities of drug overdose. Even with targeted application of agents to induce a localized thiamin deficiency, it is always possible that an overdose could occur and produce more widespread effects than intended. With most chemotherapeutic agents, once the agent is introduced there is no ready antidote. A fortunate feature of our proposed therapies is that an effective antidote (i.e., thiamin) to thiamin-deficiency therapies is readily available, and can be applied quickly in large, nontoxic, inexpensive, easily administered doses, even after symptoms of thiamin deficiency appear. (Fulton et al., supra)

Many have reported the remarkably rapid recovery of animals and of people from thiamin deficiency, even after dramatic symptoms develop. For example, Peters describes the development of symptoms of thiamin deficiency in pigeons, up to convulsions and head retraction, and notes that these symptoms "could be cured in a matter of minutes when thiamin was injected into the subarachnoid space in the brain" (Peters, 1963). In humans, Platt describes how acute beriberi patients usually recovered within a few hours after being given a few milligrams of thiamin (Platt, 1967). All these observations fit our in vitro result that cells can be brought to the brink of apoptosis by thiamin deficiency induced by thiaminase, to within hours of death, and yet show full recovery if excess thiamin is added to the culture medium.

The *Naegleria* thiaminase has been purified (Table 1, details below in Example 3) and shown to be a thiaminase I (EC 2.5.1.2), as the cleavage of thiamin is a base-substitution reaction dependent of a cosubstrate. Proof that the *Naegleria* apoptosis inducer functions as a thiaminase was obtained by cloning the gene and expressing it in *E. coli*. (see Example 3). The expressed protein had thiaminase activity that was effective at inducing apoptosis with the same latent period as the *Naegleria* agent. Apoptosis-inducing activity depends on the catalytic activity of the enzyme, since when we replaced Cys at the catalytic site of thiaminase I (see (Costello et al., 1996)) with a Ser, the replacement inactivated both the enzymatic activity and the ability of the protein to induce apoptosis (Table 2).

Thiaminase has no intrinsic toxicity to cell cultures, except due to depletion of thiamin (Lai and Fulton, unpublished data). In addition, early studies with animals showed that injected thiaminase of a mollusk remained in mice and rats without showing intrinsic toxicity, but caused a thiamin deficiency when administered parenterally for a week ((Ostrovsky et al., 1988; Puzach and Ostrovsky, 1976)).

Thiaminases are very effective at reducing thiamin concentrations, showing the amplifying power of a catalyst such that one thiaminase molecule can destroy many thiamin molecules. The *Bacillus thiaminolyticus* thiaminase I has a $k_{cat}$ of 34 $s^{-1}$ (Costello et al, 1996). Our first estimates using the *Naegleria gruberi* thiaminase I expressed in *E. coli* have given a $K_{cat}$ of ≈100 $s^{-1}$ (N. Kuperwasser, E Lai and C. Fulton, unpublished data).

We here present our *Naegleria* thiaminase gene sequence and the deduced amino acid sequence of its gene product (thiaminase protein) expressed in *E. coli* (FIGS. 4-6). This expressed protein possesses thiamin-cleaving enzymatic activity and it is a potent death-inducing agent in its ability to induce apoptosis in vertebrate cells. In extracts made of the enzymes expressed in *E. coli*, the death-inducing activity of the *Naegleria* enzyme has been found to be 1000-fold higher than that of *Bacillus* thiaminase I; the extracts are active at dilutions of $10^{-7}$ and $10^{-3}$, respectively. Some of this difference may be due to differences in the amount of enzyme produced in the two expression systems or to differences in the stability of the enzymes. As little as 50 pg/ml of partially purified, expressed *Naegleria* thiaminase was able to induce apoptosis of C6 cells in culture (see Example 2, below) in 4.5 days.

This report of the *Naegleria* thiaminase gene sequence provides us with a vector to transform live bacteria, which in turn can express the *Naegleria* agent, thiaminase I, that induces delayed apoptosis. Using methods familiar to those practiced in the art, these thiaminase gene products can be coupled to various ligands, or the coupling can be engineered at the DNA level and then expressed. The thiaminase can also be expressed in non-pathogenic bacteria designed to target to tumor sites (Example 6, below), where thiaminase can be utilized to induce apoptosis in the cancer cells. In addition, the finding of the expressed gene product allows us to mass-produce *Naegleria* thiaminase in *E. coli*. This thiaminase can then be coupled in vitro to tumor-specific antibodies or other elements (see Pat1) to be targeted to tumors in vivo. The genes can also be used in various methods of gene therapy.

Example 1

Assays for Thiaminase Activity 1-1. Measurement of thiaminase in liquid. Thiaminase activity was determined as described by others (e.g., (Costello et al., 1996)). In the case of thiaminase I, which depends on a base substitution reaction, a secondary nucleophile is used. The absorbance change at 252 nm, resulting from the reaction of thiamin with the secondary nucleophile (aniline), was monitored ((Lienhard, 1970)). The assay mixture contained 0.93 mM aniline, 0.093 mM thiamin, 100 mM sodium phosphate buffer (pH 6.5), and 2 mM dithiothreitol in a 1 ml volume at room. temperature. The assay was initiated by addition of enzyme or sample and monitoring the change in absorbance at 252 nm at 0 min and 10 min. The activity was calculated according to the following equations ((Costello et al., 1996)) where A=absorbance change at 252 nm, V=total assay volume in microliters, $\epsilon$=the difference between the sum of the extinction coefficients of the products and the sum of the extinction coefficients of the reactants (11,200 $M^{-1}$ $cm^{-1}$ (aniline), 2,415 $M^{-1}$ $cm^{-1}$ (veratrylamine)), l=path length of the cuvette, t=assay time, and p=protein in milligrams.

Activity ($\mu$mol/min)=($\Delta A$)($V$)/($\Delta\epsilon$)($l$)($t$).

Specific activity ($\mu$mol/min/mg)=($\Delta A$)($V$)/($\Delta\epsilon$)($l$)($t$)($p$).

One unit of thiaminase is defined as the amount of enzyme that will produce 1 $\mu$mol of product per min at 25° C.

Other methods of assay are available. For both thiaminase I and II, one can also measure the amount of thiamin that remains using the thiochrome method (see Wyatt et al., 1989), or measure the degradation directly using thiamin that is radioactively labeled in the thiazole ring (Evans, 1975; Edwin, 1979; Alston and Abeles, 1987).

1-2. Visualization of thiaminase on a solid support. Detection of thiaminase on solid supports, such as agar or polyacrylamide gels, can be achieved by a simple staining procedure which involves detection of residual thiamin by a colorimetric assay using a diazo coupling reagent ((Abe et al., 1987)). Diazo reagent was prepared as described ((Abe et al., 1986)). Wherever thiamin is present the gel. support turns pink, whereas where thiamin is absent (e.g., destroyed by thiaminase), the gel is colorless.

The following protocol is specifically for detection of thiaminase following polyacrylamide gel electrophoresis. The gel after electrophoresis and subsequent wash was placed in a solution of 1 mg/ml thiamin, 1 mg/ml aniline (Fisher, distilled, 1 mg=0.978 $\mu$l), 2 mM dithiothreitol, and 25 mM sodium phosphate buffer (pH 6.5) at room temperature for 10 min, and then the solution was discarded. Residual excess of the solution on the gel surface was absorbed with a filter paper and incubated at 37° C. for 30 min in a covered box. The degradation of thiamin was detected by the diazo coupling reaction as described below.

The diazotized p-aminoacetophenone mixture was poured on the gel that had completed the incubation as described above (16 ml for 5 min, then an additional 16 ml for another 5 min, against 26 $cm^2$ of gel surface). After 10 min at room temperature, the solution was decanted. The diazo group couples to the thiamin and turns the background of the gel into a reddish-pink color. When thiaminase catalyzes the substitution reaction between thiamin and aniline, the diazo reagent is not able to couple to the free thiazole or the substituted base covalently linked to the pyrimidine ring, resulting in a "white halo" on the pinkish gel.

Example 2

Functional Test for Apoptosis-Inducing Activity In Vitro

Many cell lines can be utilized for assay of the apoptosis-inducing activity of thiaminase. The following protocol describes the use of C6 rat glioma cells, but would be equally applicable, e.g., to HeLa human cervical carcinoma cells.

C6 rat glioma cells were plated at $1\times10^5$ cells/ml in medium 199 containing 10% fetal bovine serum and 50 $\mu$g/100 ml gentamicin and a dilution of agent or extract to be tested was added at the time of plating, designated day 0. Assays were conducted under various conditions, e.g., 1 ml per well in a 24-well multiwell dish. The cultures were observed at ~12 hour intervals. The latent period was scored by noting when cell death created about 25% open space in the culture, as readily evaluated visually, and the time of apoptosis noted.

*Naegleria* cell extracts were prepared by harvesting and resuspending the cell pellet in 10 volumes of sterile demineralized water, followed by three freeze-thaw cycles, centrifuging the suspension, and filtering the supernatant through a 0.22 $\mu$m pore size Millipore filter. Dilutions of cell extracts continue from this $10^{-1}$ solution. Dilutions of cell extracts were added to each well. Cells were allowed to grow at 37° C. in 95:5 air:$CO_2$.

Example 3

Purifying Thiaminase from *Naegleria*, Cloning and Expressing its Gene, and Testing for Enzyme Activity and Apoptosis-Inducing Activity Purification of Thiaminase.

The strategy used for purification of *Naegleria* thiaminase, with the results of a sample purification, is outlined in Table 1. The original preparation of the *Naegleria* apoptosis-inducing agent used three cycles of freeze-thaw ((Dunnebacke and Schuster, 1971)); this procedure was modified for preparation of *Naegleria* extract, Nex, and as a first step in the purification of the apoptosis-inducing agent.

3-1. Freeze-thaw. Sixty baking trays of *Naegleria gruberi* strain NEG ((Fulton, 1970)) amebae ($6\times10^{10}$ cells) ((Kowit and Fulton, 1974)) were harvested, washed three times by centrifugation (900×g at 4° C. for 1 min) and centrifuged into a pellet, with all supernatant decanted. These pellets could be prepared from two batches of 30 trays each and stored at −70° C. until use. The cell pellets were suspended in 10 volumes of Dialysis Buffer (50 mM Tris.HCl, pH 7.5, 2 mM dithiothreitol, 2 mM EDTA (ethylenediaminetetraacetic acid)) and subjected to four cycles of freeze-thaw at −72° C. (dry ice-ethanol) and 22° C. (water bath). The lysate after the freeze-thaw step was centrifuged for 30 min at 4° C. at 9000 rpm (6000×g) using a Beckman JA-20 rotor. The supernatant was used for the next step.

3-2. Ammonium sulfate fractionation. The supernatant was adjusted to 50% saturation by the slow addition of solid ammonium sulfate (to 291 g/l) at 0° C., stirred for 1 h at 0° C. and centrifuged at 11000 rpm (9500×g) at 4° C. for 20 min. The supernatant was then brought to 70% saturation by the addition of solid ammonium sulfate (an additional 125 g/l) at 0° C. and stirred for 1 h before centrifugation at 9500×g for 20 min at 4° C. The resulting pellet of material soluble in 50% but insoluble in 70% ammonium sulfate was dissolved in 10-24 ml of Dialysis Buffer (using the smallest volume in which the entire sample appeared to dissolve), and dialyzed in the same buffer in the cold room overnight with two changes of buffer, 1 liter each. 3-3. DEAE fractionation. The dialyzate was filtered using first a 0.45 μm Millex-HA sterile filter (Millipore Corp.) and then a 0.22 μm Millex-GV sterile filter. The sample was loaded onto a DEAE-ion exchange (Whatman DE 52 pre-swollen microgranular anion exchanger diethyl aminoethyl cellulose, catalogue no. 4057-050) column (Glenco 32 cm×28 mm (inside diameter)) equilibrated with Dialysis Buffer at a pump flow rate of 1.4 ml/min using LKB VARIOPERPEX® The column was washed thoroughly with the same buffer to remove unbound protein. The protein was eluted using a sodium chloride step gradient of 0 to 0.3 M NaCl. The fractions containing thiaminase activity were pooled, and concentrated by ultrafiltration (Amicon, PM-10) (Amicon, Beverly, Mass. 01915). The protein was dialyzed in a BioCad Buffer (20 mM Tris/BIS-propane [80% pH 6.0, 20% pH 9.0], 2 mM dithiothreitol) at 4° C. overnight with two changes of buffer, 1 liter each.

3-4. PerSeptive high-speed perfusion (column) chromatography. The dialyzed sample was loaded onto a 4.6 mm diameter, 100 mm long column containing a POROS® 20 HQ Media packed according to manufacturer's instructions and fractionated using a BiOCAD™SPRINT™ Perfusion Chromatography® System and an ADVANTEC SF-2120 Super fraction collector. The fractions containing thiaminase activity were pooled and dialyzed against 2 mM dithiothreitol in the cold room overnight with 2-3 changes of buffer, 1 liter each.

3-5. Preparative IEF (isoelectric focusing). The sample was further purified using the technique of preparative IEF, which utilizes a Bio-Rad Rotofor (model 3000Xi computer controlled electrophoresis) and Bio-Rad RotoLyte pH range 3.9-5.6. The fractions containing thiaminase activity were pooled and dialyzed in Tris/DTT buffer (50 mM Tris.HCl, pH 7.5, 2 mM dithiothreitol) in the cold room overnight with 2 changes of buffer, 1 liter each. The dialyzed sample was concentrated using a Microcon-10 (10,000 MW cut-off) (Amicon).

Figure 3:
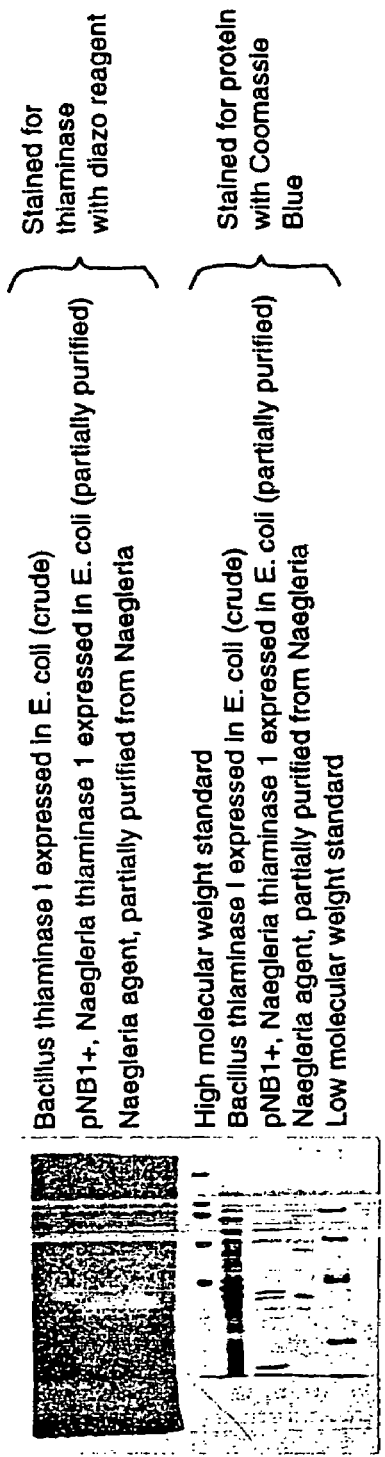
FIG. 3 shows the staining of a polyacrylamide gel of partially purified *Naegleria* agent using the diazo reagent. The clear area indicates the band that contains thiaminase.

3-6. Laemmli SDS-polyacrylamide gel electrophoresis. The partially purified sample of thiaminase after the preparative isoelectric focusing step was further analyzed by Laemmli SDS-polyacrylamide gel electrophoresis using a 10% polyacrylamide gel. Duplicate sets of samples including protein size standards were run on one gel. After electrophoresis, one-half of the gel was stained and destained. The other half of the gel was washed with 200 ml of 25 mM sodium phosphate buffer (pH 6.5) with slow stirring to remove SDS at room temperature with two changes of buffer for 20 min each. The thiaminase band(s) on the gel was detected colorimetrically using a diazo coupling reagent (Example 1-2, above). An example of this visualization is shown in FIG. 3.

To visualize protein bands, the gel was stained after the diazo coupling reaction with 0.1% Coomassie blue R250 in water/methanol/acetic acid (5:5:2). This procedure allowed the verification of the band with thiaminase activity to be stained by a protein stain.

Although precise means to determine the amount of thiaminase I enzyme in *Naegleria* are not yet available, on the basis of the amount recovered during purification and the documented losses (Table 1), we estimate that thiaminase I accounts for about 0.01% of the total protein of the amoebae.

The band of protein with thiaminase activity was excised from the gel, rinsed with 50% acetonitrile, and sent to Harvard Microchemistry Facility (Harvard University, Cambridge, Mass.) for microsequencing in order to obtain sequences of peptides to seek and identify the thiaminase gene.

3-7. Microsequencing. The protein was enzymatically digested and analyzed by HPLC chromatography. Peptides were selected and further analyzed by matrix-assisted desorption time-of-flight mass spectrometry (MALDI-TOF MS) performed on a PerSeptive BioSystems Voyager-DE STR (Framingham, Mass.) ((Chait and Kent, 1992)). These peptides were sequenced with high confidence as supported by MALDI result.

Cloning the *Naegleria* Thiaminase Gene 3-8. Genomic clone isolation. Three peptide fragment sequences derived from analysis of the gel purified putative thiaminase were obtained. Peptides A (SEQ ID NO: 12) (ASDLPQSGDQVNK), B(SEQ ID NO: 13) (TILDSTVVASQR), and C(SEQ ID NO: 14) (SSNFYAQLSQQFDAK) were compared to the peptide sequence of *Bacillus subtilis* thiaminase I precursor to determine the best estimated local alignment for each fragment using LALIGN (FASTA v.2.0u54 (X. Huang and W. Miller (1991) Adv. Appl. Math: 12:337-357)). Sets of forward and reverse degenerate oligonucleotide primers were designed based on these alignments, and synthesized using an Expedite™ model 899 DNA synthesizer using phosphoramidite synthesis chemistry (PerSeptive Biosystems, Framingham, Mass.). Peptide A forward primer AF1(SEQ ID NO: 15) (5'-CARWSIGGHGAYCARG-3') and peptide C reverse primer CR1(SEQ ID NO: 16) (5'-TTIGCRTCRAAYTGYTG) generated an amplimer of ~400 by as expected based on the *B. subtilis* alignments, was designated AC400 and chosen for gel purification using a QIAEXII gel purification kit (QIAGEN, Santa Clarita, Calif.). Fluorescent DNA sequencing reactions using the CR1 degenerate oligonucleotide and the gel purified AC400 PCR DNA fragment were performed using an Applied Biosystems 373 Stretch DNA Sequencer, and ABI PRISM™ dye terminator cycle sequencing reagents using DNA polymerase FS following manufacturer recommendations (PE Biosystems, Foster City, Calif.). The resulting sequence facilitated the design of two homologous internal oligonucleotides a forward primer AC1(SEQ ID NO: 17) (5'-TGTCGGATAT-AGTGAAAGTATG-3') and a reverse primer AC2(SEQ ID NO: 18) (5'-AACCTTTTGCTTTTCATCACAC-3'), which were used to complete the 431 by DNA sequence of AC400 that encodes a peptide with strong homology to *B. subtilis* thiaminase I precursor. AC400 was labeled using the random hexamer primer method and used to screen a *Naegleria gruberi* strain NEG EMBL3 genomic DNA library ((Lai et al., 1988b)), with each of the positive clones sequenced with oligonucleotides AC1 and AC2. The resulting genomic clone TTK containing all of the 431 by of the AC400 hybridization probe was chosen for more extensive DNA sequence analysis using oligonucleotide primers.

3-9. Sequence analysis and expression cassette construction. Analysis of 3414 by of genomic sequence from TTK defined an ORF of 3078 by (FIG. 4) encoding a 1025 amino acid peptide of MW 112,141 daltons (FIG. 5), with the amino terminal domain amino acid residues Met1 to Leu356 encoding a peptide of MW 39,079 daltons having strong homology to *B. subtilis* thiaminase I precursor. This homology is shown is FIG. 8, as well as the positions of the three peptide sequences from *Naegleria* thiaminase that were used to find the gene. This region was chosen for expression in pET-22b (+), with the expression cartridge generated by PCR amplification of TTK target DNA using pfu polymerase (STRATAGENE, La Jolla, Calif.). An NdeI site was introduced at the ATG start codon using a forward primer CDA1(SEQ ID NO: 19) (5'-GAGATATACAT ATGTCCACTCAACCAAAGAC-3'), and a TAA stop codon followed by a BamHI site was introduced after Leu356 using the reverse primer CDA2(SEQ ID NO: 20) (5'-TATGGATCC TTAAAGGAATGGTCTCAAGACACC-3'). The resulting 1091 by amplimer was digested with NdeI and BamHI, gel purified and the expression cassette ligated into pET-22b(+) followed by transformation into *E. coli* XL1-blue™ (STRATAGENE, La Jolla, Calif.). Sequencing of the resulting plasmid pNB1+ verified the expected 1068 by ORF (FIG. 6) including the potential catalytic Cys118, as well as the junctions essential for expression of the 356 amino acid MetlLeu356 peptide (FIG. 7).

Expressing *Naegleria* Thiaminase in *E. coli*

3-10. Expression and functional selection. Expression and functional selection were based on enzymatic activity of colonies on agar (Example 1). The recombinant pET-22b(+) plasmid (Promega, Madison Wis.), containing the 1068 by (base pair) NdeI-BamHI fragment encoding the *Naegleria* thiaminase gene sequence was isolated and purified from *E. coli* XLI-blue™ strain, and subsequently used to transform *E. coli* BLR(DE3)pLysS (Novagen), or BL21(DE3)pLysS (Novagen). The positive clones were selected on agar by the same diazo coupling reagent as discussed above (see Section 3-6). This assay is based on the abilities of the clones to synthesize functional thiaminase that could cleave thiamin in situ on agar (Abe+86). These positive clones were further confirmed by preparing freeze-thaw cell extracts and assaying for their thiaminase I activity using the spectrophotometric method mentioned above (see Example 1-1) and by performing a cell death assay on rat glioma C6 cells (Example 2). A clone that produced a high level of thiaminase was designated pNB1.

Site-Directed Mutagenesis of Thiaminase I 3-11. PCR site-directed mutagenesis. PCR site directed mutagenesis of the potentially catalytic cys118 codon (TGC) to ser118 (AGC) was performed using a variation on the method of Barettino et al. (1994) N. A. R. 22(3):541-542. The position of the catalytic Cys codon is shown in FIG. 8. A mutagenic coding strand (reverse) primer CDA3 (SEQ ID NO: 21) (5'-CAA TAA AAA GTT TGA GCT CAA GTA TTG-3') was used in conjunction with the forward primer CDA1 to amplify a 380 by mutagenic megaprimer. Following gel purification the megaprimer was extended using the reverse primer CDA2 in a linear PCR extension reaction. The resulting 1091 by fragment, containing a GCT (encoding Ser) instead of GCA (encoding Cys118) was digested with NdeI and BamHI, subcloned, sequenced and expressed as detailed above. The resulting mutant clone, named pNB1-S, was confirmed to have a Cys118Ser substitution, and it tested negative for enzymatic activity on agar, in the spectrophotometer, and by a cell death assay. The result of this experiment is listed in Table 2.

Example 4

Cloning and Sequencing of Other Thiaminase Genes

The cloning and sequencing of other thiaminase genes can be accomplished by one or more of the following methods. The methods are listed in the order of the ease of their performance. If the first method proves not applicable, the second method should be tried, and so on.

*Naegleria* thiaminase I, as isolated in *Naegleria* extract and as expressed in active form in pNB1+(FIGS. 6-7), has a molecular weight of ≈40,000, similar to the *Bacillus thiaminolyticus* enzyme, which is 42,000 ((Costello et al., 1996)). A comparison of the sequences of these two enzymes is given in FIG. 8. The normal isolation protocol for the *Naegleria* enzyme involves repeated cycles of freezing and thawing. This protocol also releases all the proteases of this "bacteria-eating" amoeba, and in our extensive experience with this organism few proteins survive this harsh procedure. The survival of *Naegleria* thiaminase Ito repeated freeze-thaw cycles is an indication of the remarkable stability of this protein to proteolytic enzymes, a useful attribute for potential therapeutic use in vivo. In *Naegleria* the thiaminase is encoded as segment of a protein of ≈110 kDa (FIGS. 4-5). We have been able to detect this protein, with thiaminase activity, using protocols other that freeze-thaw to lyse the amoebae. The function of the thiaminase portion of the protein in living *Naegleria* (or any organism) is quite unknown. It is unlikely that thiaminases are active in living cells ((Fujita, 1954)), and it is even possible that this segment possesses a function distinct from cleaving thiamin, especially when in association with the rest of the encoded protein. Mollusks and ferns also have thiaminase I proteins whose molecular weights have been estimated at 93-100 kDa ((McCleary and Chick, 1977)), so in other eukaryotes it is possible that the entire protein, and not just the segment encoding thiaminase I, may prove homologous to the *Naegleria* protein.

4-1. Homologous Sequences

Based on the literature, sequences obviously homologous to the *Naegleria* gruberi strain NEG thiaminase I sequence can be expected to be readily found in, and obtainable from, organisms including: other species and strains of *Naegleria*; certain plants, especially ferns such as bracken and nardoo; some molluscs, such as clams; certain fish, especially carp, and certain bacteria other than *Bacillus thiaminolyticus*. No sequences from any such organisms have been characterized, but based on available information, and comparison of the *Naegleria gruberi* and *Bacillus thiaminolyticus* sequences (FIG. 8), these thiaminases are anticipated to be clear homologues. It is advantageous to have isolated, purified, or enriched nucleic acid sequences encoding such thiaminases for use in the present invention. Such nucleic acid sequences can be obtained using routine techniques known to those skilled in the art.

We claim as homologues any protein, and any gene that encodes a protein, with the following characteristics, and any derivative of such a protein useful in relation to apoptotic therapies:

1) Thiaminase I activity in its wild-type form. Mutation in vivo or in vitro to catalytically inactivate the protein does not remove the protein or its genes from homologous status.

2. Overall similarity of the amino acid sequence over the entire length of the thiaminase I protein, or the thiaminase I segment of a larger protein. This similarity can be established by comparing the thiaminase I encoded by pNB1 (FIG. 7) with the overall amino acid sequence in question using the FASTA program ((Pearson and Lipman, 1988)). Currently, in September 1999, using the amino acid sequence of *Naegleria* thiaminase I (FIG. 5) to search the non-redundant protein library (NCBI database), with default parameters, yielded the *Bacillus* thiaminase I with ≈25% identity in a 358 amino acid overlap. No other proteins that showed strong identity over a long overlapping sequence. A suitable criterion for a putative thiaminase would be >22% identity over 300 amino acids.

3) Local similarity to active site regions as determined by BLAST. For example, the catalytic domain segment of 13 residues surrounding the active site Cys, (SEQ ID NO: 22) VYGFPQYLCSNFL, would be expected to give an identity of 8 of the 13 amino acids (see FIG. 8).

Once candidate thiaminases are recognized by these criteria, they can be expected to show other features. One example is the six amino acid sequence (SEQ ID NO: 23) GYSESM that starts at residue 228 of *Naegleria* thiaminase I (FIG. 7). This is part of the pyrimidine coordinate residues, and one would expect a match of $\leq 5$ of the 6 residues.

4-2. Direct PCR Method

In one approach, using procedures known to those skilled in the art, the amino acid sequence can be used to design DNA primers, and these can be used in conjunction with the polymerase chain reaction (PCR) to identify the corresponding thiaminase gene (genomic or cDNA sequences) (Mullis et al., 1994). Preferably, amino acid sequences are used which correspond to unique or low degeneracy primer sequences. Genes will be cloned, sequenced, and expressed using standard techniques (Sambrook et al., 1989). Total DNA is prepared from the organism whose thiaminase gene one wishes to clone. Standard methods known to those experienced in the art can be used ((Sambrook et al., 1989)), and specific methods have been developed for plants and especially for ferns ((Dempster et al., 1999)). Oligonucleotide primers will be designed based on our knowledge of *Naegleria* thiaminase I gene sequence (FIGS. 6-7), comparison with the *Bacillus thiaminolyticus* sequence (FIG. 8), and knowledge of codon-usage patterns in the organism in which the gene is being sought. These primer sets will be used to prime PCR reactions in order to locate the gene of interest. Additional oligonucleotide primers will be prepared to allow extensive sequencing of the whole gene, as well as cloning it (see example in Sections 3-8 to 3-10).

4-3. Using the *Naegleria* Thiaminase Gene as a Heterologous Probe

The *Naegleria* thiaminase gene can be used as a heterologous DNA probe to screen for thiaminase genes in other organisms. Total genomic DNA will be prepared from any organisms to be screened for thiaminase (as in Section 4-2, above). To determine if there is sufficient homology between the *Naegleria* thiaminase gene and those being sought, a pilot Southern blot experiment will be performed. It is recognized that the apparent homology can be affected by introns, which are absent in the *Naegleria* thiaminase gene but may be present in others. The total genomic DNA is digested with restriction enzymes, the digested products are run on a DNA agarose gel, then transferred onto nitrocellulose ((Southern, 1975)). The *Naegleria* thiaminase gene is $^{32}$P-labeled by random hexamer primer labeling and used as a probe to hybridize to the DNA on the nitrocellulose using non-stringent hybridization conditions we developed ((Lai et al., 1988a)). A positive signal on the autoradiograph would indicate that sufficient homology exists between the *Naegleria* gene and the desired gene. A phage lambda genomic library would be constructed using total DNA of the organism of interest. The *Naegleria* thiaminase gene will be used as a heterologous probe to screen these libraries for the desired thiaminase gene.

4-4. cDNA Expression Cloning

Total mRNA will be extracted from the organism of interest, and a cDNA expression library constructed using standard procedures (as (Sambrook et al., 1989). Colonies expressing the thiaminase gene will be sought using the diazo reagent method in agar (see Sections 1-2 and 3-10).

4-5. Purification of Thiaminase Protein-Followed by Microsequencing of the Proteins, Cloning, and DNA Sequencing Thiaminases can be purified by following the methods described in the literature (see Fulton et al, supra, for an extensive review), as well as our more current methods described in detail here (Sections 3-1 through 3-7). Thiaminases can also be purified using standard methods used by other workers (Deutscher, 1990; Menge, 1994; Costello et al., 1996). In early studies, fish thiaminase ((Ågren, 1945; Ågren, 1946)), clam and mussel thiaminases ((Alston and Abeles, 1987; Fujita, 1955; McCleary and Chick, 1977)), fern thiaminases ((Kenten, 1957; McCleary and Chick, 1977)), and thiaminases of *Clostridium sporogenes* and *Bacillus aneurinolyticus* ((Ikehata, 1960; Kobayashi, 1975; Wittliff and Airth, 1970)) have been partially purified. Purification can be monitored by assays of thiaminase activity (Section 1-1 and 1-2), evaluations of protein purity by gel electrophoresis (Section 3-6), and assays of death-inducing activity (Example 2). Once the purified thiaminase protein is available, it will be microsequenced to obtain partial peptide information (as Section 3-7). Oligonucleotides will be designed and prepared based on peptide sequence information, and used for screening a genomic DNA or a cDNA library (as Section 3-8). The resulting positive clone(s) will be sequenced to confirm that it encodes a thiaminase (as Section 3-9). These clones will subsequently be expressed in *E. coli* and the expression clones selected using the diazo coupling reagent in agar (see Section 3-10). Cell extracts will be prepared from these clones and the thiaminase enzyme activity will be determined as described (Example 1). Cell death assays will be performed as described (Example 2).

Example 5

Targeting Thiaminase for Localized Delivery

Effective therapeutic use of thiaminase is likely to require localizing the thiaminase to target cells or tissues, since an overall thiamin deficiency would cause the various symptoms of beriberi. Many means are available for targeting thiaminase, as detailed in Fulton et al., supra. These include the following examples, all described in detail in Fulton et al., supra, all familiar to those in the field of cancer therapy:

1) Localized administration, e.g., upstream of a capillary bed feeding a tumor.

2. Targeting by coupling thiaminase to an antibody or an antibody derivative that will carry it to the desired cells or tissues.

3. Targeting by coupling thiaminase to a targeting receptor ligand.

4. Targeting by binding thiaminase to a liposome or other delivery vehicle that will target it to the desired cells.

5. Targeted gene therapy using thiaminase, e.g., using a hypoxic response element that will express the thiaminase gene in the hypoxic regions of solid tumors.

6. Target using nonpathogenic bacteria to see tumors and there express thiaminase.

7. Making the enzyme inactive until localized, by depending on a property that would activate the enzyme in the target tissue (such as using the protease activity of prostate specific antigen to turn on the enzyme in prostate tumor tissue).

8. Target the enzyme (e.g., by using bacteria as a warhead) to specific cavities in the body, such as the bladder or the colon.

9. Target to the lung by pulmonary absorption.

In connection with these various targeting techniques, those skilled in the art will recognize that such targeting can be utilized for both the administration of thiamin-depleting agents and for the administration of nucleic acid sequences encoding thiamin-depleting agents.

Example 6

Thiaminase Carried by Non-Pathogenic Bacteria Used for Prostate Cancer Therapy

It is instructive to consider one example of specific targeting of thiaminase for therapy of a specific cancer. The example chosen is the use of thiaminase carried as a warhead on a non-pathogenic bacteria that will seek and attack metastatic prostate cancer. It will be evident that this example could easily be applied to other types of cancer and to other methods of localizing thiaminase or its genes.

Prostate cancer is responsible for 43% of new noncutaneous cancer cases in men, and has become the second leading cause of male cancer deaths (da Vita, 1997, pp. 1322-1386). The tumor cells in the adenocarcinomas are initially androgen dependent, and androgen ablation (e.g., castration) causes apoptosis of these cells. This causes initial remission of the prostate cancer, but any tumor cells left behind eventually change from androgen-dependent to androgen-independent (see Umekita et al., 1996). Thus after an initial remission as the androgen-dependent cells die, within a year or two the androgen-independent cancer cells become evident, grow, metastasize, and eventually kill the patient. The major problem in devising a therapy to kill these androgen-independent, metastatic tumor cells has been that most of the cells are not actively proliferating at any particular time; it has been estimated that about 2% undergo division on any given day. As J. T. Isaacs and his coworkers put it, "Unfortunately, more than 90% of prostatic cancer cells within an individual patient are in interphase" (Kyprianou et al., 1991). These authors concluded that the only hope to improve survival rates for prostate cancer is simultaneous therapy of androgen ablation to kill the androgen-dependent cells and some therapy to eliminate the androgen-independent cells. One way to eliminate the androgen-independent cells is to increase the rate of apoptosis among non-proliferating cancer cells.

Prostate cancer provides an excellent situation for use of thiamin-depletion-induced apoptosis. The many cells lines in which the *Naegleria* agent (thiaminase I) was shown to induce apoptosis include two cell lines derived from human prostate cancers, LNCaP, which is an androgen-dependent cell line with a functional p53 gene, and PC-3, which is an androgen-independent cell line that is null for the p53 gene. Thus, prostate cancers are among good candidates for treatments using our invention. In order to induce apoptosis in these cancer cells, it would suffice to surround the cells, the tissues, or the tumors with thiaminase, and thereby starve the cells for thiamin.

For this therapy it is important to maintain the low level of thiaminase continuously around the cancer cells until the cells become depleted of the vitamin and undergo apoptosis. The therapy does not require that every cell be surrounded. Adequately surrounding a group of cells (e.g., a solid tumor) would be sufficient. A particularly useful approach would be to localize the thiaminase by lining the walls of the capillaries that feed the prostate cancer cell mass, thus destroying all thiamin brought to the tissue. The principle of this method is to surround the cancer cells and starve them of thiamin until they all undergo apoptosis. Properly applied, this therapeutic approach could avoid the widespread nonspecific tissue damage that accompanies use of poisons and radiation. While one could use antibodies or other targeting ligands to carry the thiaminase to the cancer, there are advantages to using non-pathogenic bacteria.

Bacterial infections of tumors, sometimes associated with regression of the tumors, have been known for two centuries ((Nauts et al., 1953; Wiemann and Starnes, 1994)). There have been many reports of the use of living bacteria for cancer therapy (reviewed in Minton and Oultram, 1988; Pawelek et al., 1997; Saltzman et al., 1997). In one frequent use, since 1976, attenuated "bacille Calmette-Guèrin" (BCG) has been instilled intravesically into bladders to reduce recurrence of bladder cancer. The procedure offers benefit (e.g., Lamm et al., 1991).

One especially notable approach involves the use of *Salmonella* spp., especially *S. typhimurium*, for cancer therapy (e.g., (Low et al., 1999; Pawelek et al., 1997; Saltzman et al., 1997)). For example, it was found (Pawelek et al., 1997) that attenuated (non-pathogenic) hyperinvasive, polyauxotrophic mutants of *S. typhimurium* targeted melanomas in mice, and in vivo reduce the rate of tumor growth and increased survival to as much as twice the survival time of uninfected-mice. The bacteria were found at high concentrations in the tumors, both in the necrotic zone of the tumors and inside cells.

The advantageous attributes of *Salmonella* as a living vector to deliver thiaminase to a tumor include:

1. known affinity of *Salmonella* for tumors, and growth therein;
2. presence on these bacteria of systems for invading vertebrate cells;
3. ease of culture;
4. facultative anaerobe, able to grow both aerobically and anaerobically, whether in culture or in tumors;
5. ease of isolating mutants, e.g., attenuated, hyperinvasive, or auxotrophs;
6. availability of the extensive, powerful genetics and molecular biology techniques of enteric bacteria; and
7. extensive knowledge of the pathogenicity of this species.

To use this system for thiamin-deficiency therapy, attenuated, hyperinvasive bacterial strains that efficiently express and secrete thiaminase are engineered, using well known molecular biology techniques. These bacteria would be injected into animals bearing tumors, where they would preferentially locate and grow in the tumors, both intracellularly and extracellularly. The thiaminase produced by those bacteria would cause LAIDT. As with other methods of causing LAIDT, this treatment can be combined with other therapies.

Another example of the use of bacteria as tumor-specific, amplifiable protein expression vectors is the use of an anaerobe to specifically target the hypoxic environment of tumors. While cells at the surface of a tumor mass often are actively proliferating and usually susceptible to radiation and chemotherapy, the central cells, in addition to being inaccessible, are largely not proliferating and stubbornly resistant to therapeutic treatments (Hickman et al., 1994). The centers of such solid tumors are often hypoxic (oxygen deficient), an environment that favors selection of cells that express bcl-2 but not p53 and thus become highly resistant to apoptosis induced by currently used therapeutic agents (Graeber et al., 1996). Hypoxia in these tumor masses is correlated with insensitivity to non-surgical therapies and a poor prognosis for successful control of the cancer and for patient survival. The presence of hypoxic tumors was a strong predictor of probable disease recurrence and of poor survival (Höckel et al., 1996).

Based on in vitro studies, it is anticipated that sustained thiamin depletion will induce apoptosis in the non-cycling "dormant" cells of solid tumor masses. In addition to the possibility of "surrounding" tumor masses with a thiamin-cleaving compound, another approach to LAIDT uses anaerobic bacteria as carriers.

Spores of *Clostridium* species have long been known to exhibit remarkable specificity for solid tumors. The spores become localized in, germinate, and grow in the hypoxic tissue (reviewed in Minton et al., 1995). This unique property can be used to locate solid tumors in the body as well as to target therapeutic agents. Even nonpathogenic species kill some of the cancer cells, but infection alone is not sufficient to kill the tumor. For example, *C. butyricum* M-55 injected intravenously or intratumorally caused tumor lysis after 5-8 days, in some cases leaving only the outer rim of cancer cells (which regrew) (e.g., Möse and Möse, 1959; Heppner and Möse, 1978). Any associated toxemia could be controlled with antibiotics.

Recently, avirulent *C. beijerinckii* have been genetically engineered to express enzymes that would cleave prodrugs (Minton et al., 1995; Fox et al., 1996), and techniques for genetic engineering of Clostridia have been developed (Rood et al., 1997). Animals bearing solid tumors are injected with these Clostridia, and, after the bacteria have lodged in the tumors, the animals are injected with the prodrug. Cleavage of the prodrug by the enzyme secreted in the tumor targets the toxic drug to the core of solid tumor.

*Clostridium* sp. that expresses thiaminase can be used to target and infect solid tumors, and thereby induce localized thiamin deficiency. One possibility for a suitable bacterium would be the avirulent *C. sporogenes* ATCC 8075, already known to make and secrete a thiaminase I (Kobayashi, 1975a). The *C. butyricum* M-55 used in early attempts to treat tumors is now classified as *C. sporogenes* ATCC 13732, so is presumably closely related to the strain known to secrete thiaminase. An alternative possibility is to use another species of *Clostridium*, or even another genus of anaerobes. It may be desirable to genetically restrict or attenuate the bacterium used so it will accomplish the effective delivery of thiaminase and induction of apoptosis without causing unwanted sepsis. One possibility would be to use the *C. beijerinckii* currently being used in prodrug experiments (Minton et al., 1995; Fox et al., 1996), and to engineer this strain to overexpress and secrete an appropriate thiaminase.

Treatment of solid tumors with Clostridia expressing thiaminase would induce apoptosis of the central tumor mass. To assure death of the whole tumor mass the *Clostridium*-thiaminase therapy would preferably be coupled with a treatment directed at the peripheral cells, such as conventional radiation and chemotherapy or separately surrounding these cells with thiamin-cleaving compound by some other means, for example, using an antibody-thiaminase conjugate.

Example 7

Combination of Thiamin Depletion and Accessory Treatment for Targeted Cells

In addition to the use of thiamin depletion to induce apoptosis of a targeted group of cells, a variety of different accessory treatments can be utilized in conjunction with the thiamin depletion to enhance the effectiveness of the treatment. Conversely, for some treatments, such as other antineoplastic treatments, the use of apoptosis induced by thiamin depletion can be regarded as enhancing the effectiveness of that other treatment. Thus, the present invention includes such combination therapy, where thiamin deficiency induced apoptosis is used in conjunction with another treatment method. In these combination methods, the thiamin depletion can be targeted by any of a variety of methods, for example, by any of the methods described herein. Also, the accessory methods also preferably involve localized or targeted treatment. Any of a variety of methods may be used for such targeting also, again for example, the targeting methods described for targeting of thiamin depletion, with the choice of targeting method being appropriate for the type of composition involved in the accessory treatment. Those skilled in the art will readily recognize the appropriate selections, which include a variety of standard treatments involving radiation and chemotherapy.

One particularly promising therapy to combine with LAIDT is antiangiogenesis. It has been shown that the growth of solid tumors beyond about 2 mm depends on vascularization (Folkman, 1997). Recent studies have shown that inhibitors of this angiogenesis can result in tumors becoming quiescent (Boehm et al., 1997: O'Reilly et al., 1996; Skobe et al., 1997). As described above, thiamin deficiency induced apoptosis kills quiescent cells. Thus, inducing quiescence of cells in a solid tumor would markedly enhance the therapeutic effectiveness of inducing a targeted thiamin deficiency in that tumor by increasing the fraction of quiescent cells.

Antiangiogenesis therapy appears to work by disrupting the tumor microvasculature that provides nutrients, including oxygen, to a tumor and takes away waste. In that sense, antiangiogenesis therapy produces overall "starvation" of the tumor. Some cells die, apparently both by necrosis and by apoptosis, while others simply become dormant (quiescent). Overall starvation, depending on the exact (and locally variable) conditions, induces death of some cells and quiescence in others. In contrast, specific starvation for thiamin induces apoptotic death, even in quiescent cells. Thus, these paradigms differ, and are, in fact, complementary. Used together, for example, antiangiogenesis therapy can arrest cell growth and LAIDT therapy can kill the arrested cells.

A variety of antiangiogenesis compounds were described in Fulton et al., supra, and can be utilized herein.

Example 8

Use of Inactive Thiaminase and Multiple Thiaminases to Avoid Rejection

As a foreign protein, it is anticipated that thiaminase may cause an immune reaction. In previous experiments, we have shown that injection of rabbits with concentrated extracts of *Naegleria*, which we now know contained the *Naegleria* agent (thiaminase I), did not cause sickness or death, although the injections did elicit antibodies to *Naegleria* proteins (Fulton, 1970, p. 454). There is no reason to anticipate that thiaminase would be toxic to animals except by lowering the thiamin concentration. In time, however, it is likely that circulating thiaminase would lead to production of antibodies against itself. Immunosuppression and other methods can be used to extend the therapeutic window. The extent to which this might be a problem depends on how long the thiaminase needs to be present to complete its task; for example, if apoptosis is induced in a tissue as rapidly as it is induced in vitro, the treatment may be complete before production of antibodies became a problem. It also depends on the immunogenicity of the polypeptide used as well as the method and place of delivery. The potential toxicity and immunogenicity of various thiaminases and their derivatives, as well as their stability in vivo, can be monitored by regular animal testing during the development of therapeutic drugs.

In a preferred embodiment, the method includes administering an inactive analogue of the thiaminase or thiaminase derivative that shares the same epitopes, thereby inducing immunologic tolerance to the inactive and corresponding active peptides polypeptides. Preferably, the inactive analogue is not targeted to the selected group of cells. One could create tolerance in the treated individual by flooding the system with an excess of enzymatically inactive but otherwise minimally altered thiaminase (prepared by mutagenesis, as described above in Section 3-11). Often oral provision of antigen is an efficient method of inducing tolerance (Weiner et al., 1994), but antigen given parenterally in high concentrations also induces tolerance (Dixon and Mauer, 1955).

Once multiple thiaminases are available, one could avoid the immune response by simply changing from one thiaminase to another thiaminase with different antigens during therapy.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The thiamin depleting compounds and methods and accessory methods described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, using other thiamin-depleting agents, targeting methods, and/or methods of administration, and other accessory methods to be used in conjunction with thiamin depletion are all within the scope of the present invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms “comprising”, “consisting essentially of” and “consisting of” may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Thus, additional embodiments are within the scope of the invention and within the following claims.

REFERENCES

Abe, M., S. Ito, M. Kimoto, R. Hayashi, and T. Nishimune. 1987. Molecular studies on thiaminase I. *Biochim. Biophys. Acta.* 909:213-221.

Abe, M., T. Nishimune, S. Ito, M. Kimoto, and R. Hayashi. 1986. A simple method for the detection of two types of thiaminase-producing colonies. *FEMS Microbiol. Lett.* 34:129-133.

Ågren, G. 1945. On the purification of the thiamin-inactivating fish factor. *Acta physiol. Scand.* 9:306-312.

Ågren, G. 1946. On the purification of the thiamin-inactivating fish factor II. *Acta physiol. Scand.* 11:344-348.

Alston, T. A., and R. H. Abeles. 1987. Enzymatic conversion of the antibiotic metronidazole to an analog of thiamine. *Arch. Biochem. Biophys.* 257:357-362.

Berges, R. R., J. Vukanovic, J. I. Epstein, M. CarMichael, L. Cisek, D. E. Johnson, R. W. Veltri, P. C. Walsh, and J. T. Isaacs. 1995. Implication of the cell kinetic changes during the progression of human prostatic cancer. *Clin. Cancer Res.* 1:473-480.

Chait, B. T., and S. B. H. Kent. 1992. Weighing naked proteins: Practical, high-accuracy mass measurement of peptides and proteins. *Science.* 257:1885-1894.

Costello, C. A., N. L. Kelleher, M. Abe, F. W. McLafferty, and T. P. Begley. 1996. Mechanistic studies on thiaminase I. Overexpression and identification of the active site nucleophile. *J. Biol. Chem.* 271:3445-3452.

Dempster, E. L., K. V. Pryor, D. Francis, J. E. Young, and H. J. Rogers. 1999. Rapid DNA extraction from ferns for PCR-based analyses. *Biotechniques.* 27:66-68.

Dunnebacke, T. H., and F. L. Schuster. 1971. Infectious agent from a free-living soil amoeba, *Naegleria gruberi. Science.* 174:516-518.

Evans, W. C. 1975. Thiaminases and their effects on animals. *Vitamins and Hormones.* 33:467-504.

Fujita, A. 1954. Thiaminase. *Adv. Enzymol* 15:389-421.

Fujita, A. 1955. Thiaminase. *Methods Enzymol.* 2:622-628.

Fulton, C. 1970. Amebo-flagellates as research partners: The laboratory biology of *Naegleria* and *Tetramitus. Methods Cell Physiol.* 4:341-476.

Ikehata, H. 1960. The purification of thiaminase II. *J. Gen. Appl. Microbiol.* 6:30-39.

Kenten, R. H. 1957. The partial purification and properties of a thiaminase from bracken (*Pteridium aquilinum* (L) Kuhn). *Biochem. J.* 67:25-31

Kobayashi, S. 1975. Thiaminase from *Clostridium sporogenes*. I. Purification of thiaminase I. *Vitamins.* 49:45-51.

Kowit, J. D., and C. Fulton. 1974. Purification and properties of flagellar outer doublet tubulin from *Naegleria gruberi* and a radioimmune assay for tubulin. *J. Biol. Chem.* 249:3638-3646.

Lai, E. Y., S. P. Remillard, and C. Fulton. 1988a. Instability of mRNAs for flagellar tubulin and calmodulin late in *Naegleria* differentiation occurs independently of flagellar assembly. *J. Cell Biol.* 107:101a (abstr.).

Lai; E. Y., S. P. Remillard, and C. Fulton. 1988b. The α-tubulin gene family expressed during cell differentiation in *Naegleria gruberi. J. Cell Biol.* 106:2035-2045.

Lienhard, G. E. 1970. Kinetic evidence for a (4-amino-2-methyl-5-pyrimidinyl)methyl-enzyme intermediate in the thiaminase I reaction. *Biochem.* 9:3011-3020.

Low, K. B., M. Ittensohn, T. Le, J. Platt, S. Sodi, M. Amoss, O. Ash, E. Carmichael, A. Chakraborty, J. Fischer, S. L. Lin, X. Luo, S. I. Miller, L.-m. Zheng, I. King, J. M. Pawelek, and D. Bermudes. 1999. Lipid A mutant *Salmonella* with suppressed virulence and TNFα induction retain tumor-targeting in vivo. *Nature Biotech.* 17:37-41.

McCleary, B. V., and B. F. Chick. 1977. The purification and properties of a thiaminase I enzyme from nardoo (*Marsilea drummondii*). *Phytochemistry.* 16: 1'07-213.

Nauts, G. A. A. Fowler, and F. H. Bogatko. 1953. A review of the influence of bacterial infection and o bacterial products (Coley's toxins) on malignant tumors in man. *Acta Med. Stand. Suppl.* 276:1-103.

Ostrovsky, Y. M., S. S. Puzach, and Z. V. Gorbach. 1988. Activity of thiaminase I and its fragments after administration of the enzyme to the animal organism. *Biol. Zentralbl.* 107:17-20:

Pawelek, J. M., K. B. Low, and D. Bermudes. 1997. Tumor-targeted *Salmonella* as a novel anticancer vector. *Cancer Res.* 57:4537-4544.

Pearson, W. R., and D. J. Lipman. 1988. Improved tools for biological sequence comparison. *Proc. Natl. Acad. Sci. USA.* 85:2444-2448.

Puzach, S. S., and Y. M. Ostrovsky. 1976. [Antivitamin activity of thiaminase from freshwater bicuspid molluscs after parenteral administration of the enzyme to albino mice] (In Russian). *Vopr. Med. Khim.* 22:769-773.

Rood, J., B. A. McClane, J. G. Songer, and R. W. Titball. 1997. The Clostridia: Molecular Biology and Pathogenesis. Academic Press. 480 p., 481.482×489.489×486.489".

Saltzman, D. A., E. Katsanis, C. P. Heise, D. E. Hasz, V. Vigdorovich, S. M. Kelly, R. r. Curtiss, A. S. Leonard, and P. M. Anderson. 1997. Antitumor mechanisms of attenuated *Salmonella typhimurium* containing the gene for human interleukin-2: a novel antitumor agent? *J. Pediatr. Surg.* 32:301-306.

Sambrook, J., E. F. Fritsch, and T. Maniatis. 1989. Molecular Cloning: A Laboratory Manual, 2nd edition. Cold Spring Harbor Laboratory Press, Cold Spring Harbor, N.Y.

Southern E. M. 1975. Detection of specific sequences among DNA fragments separated by gel electrophoresis. *J. Mol. Biol.* 98:503-517.

Wiemann, B., and C. O, Starnes. 1994. Coley's toxins, tumor necrosis factor and cancer research: a historical perspective. *Pharmacol. Ther.* 64:529-564.

Wittliff J. L., and R. L. Airth. 1970. Thiaminase II. *Methods Enzymol.* 18:234-238.

Wyatt, D. T., M. Lee, and R. E. Hillman. 1989. Factors affecting a cyanogen bromide-based assay of thiamin. *Clin. Chem.* 35:2173-2178.

TABLE 1

Purification Strategy for *Naegleria* Thiaminase, with Sample Results of One Purification

| Fraction | Total protein (mg) | Total activity (units*) | Specific activity (units/mg) | % Yield (protein) | % Yield (activity) | Purification (fold) |
|---|---|---|---|---|---|---|
| Crude extract | 875 | 5.46 | 0.006250 | 100 | 100 | — |
| 50-70% $(NH_4)_2SO_4$ | 635 | 3.97 | 0.006257 | 73 | 73 | 1.001 |
| DEAE-ion exchange | 120 | 2.42 | 0.020179 | 14 | 44 | 3.2 |
| HQ20 perfusion | 9 | 1.48 | 0.16517 | 1 | 27 | 26.4 |
| Rotofor IEF | 0.225 | 0.425 | 1.892 | 0.02 | 8 | 302.7 |

*One unit of enzyme is the amount needed to form 1 μmol of product in 1 min at 25° C.

TABLE 2

Expressed *Naegleria* thiaminase induces apoptosis, and its apoptosis-inducing ability depends on thiaminase activity

| Expression clone[a] | Enzyme activity assayed in | | C6 cell death assay |
|---|---|---|---|
| | agar[b] | cuvette[c] | latent period (days)[d] |
| pNB1+ (wild type) | white halo | 0.415 mU | 4 |
| pNB1-S | no halo | 0.074 mU | no apoptosis |

[a]See Example 3, Sections 3-10 and 3-11.
[b]See Example 1-2.
[c]See Example 1-1. Assays were performed in 1 ml volume using 10 μl of each sample and the change in absorbance at 252 nm was measured. Absorbance was measured 10 min later and mU reported here is an average of 4 readings of each sample, which represents an increase of thiaminase activity after 24 hr of expression in *E. coli* BLR(DE3)pLysS at 37° C.
[d]See Example 2. C6 rat glioma cells were plated at 1 × 105 cells/ml in medium 199 containing 10% fetal bovine serum and 50 μg/100 ml gentamicin and a $10^{-5}$ dilution of cell extracts prepared from either of the indicated expression clones was added at the time of plating (day 0). The cultures were observed every 12 hours and the time of apoptosis noted.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The specific methods and compositions described herein as presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention. For example, those skilled in the art will recognize that the invention may suitably be practiced using a variety of different expression vectors and sequencing methods within the general descriptions provided.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is not intention that in the use of such terms and expressions of excluding any equivalents of the futures shown and described or portions thereof, but it is recognized that various modifications are possible within the scope of the invention claimed. Thus, it should be understood that although the present invention has been specifically disclosed by preferred embodiments and optional features, modification and variation a of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group. For examine if there are alternatives A, B, and C, all of the following possibilities are included: A separately, B separately, C separately, A and B, A and C, B and C, and A and C.

Thus, additional embodiments are within the scope of the invention and within the following claims.

What we claim is:

1. A eukaryotic expression vector comprising a recombinant nucleic acid sequence encoding thiaminase I from *N. gruberi*, said recombinant nucleic acid sequence as set forth in SEQ ID NO:3.

2. A vector comprising a recombinant nucleic acid sequence encoding thiaminase I from *N. gruberi*, said recombinant nucleic acid sequence as set forth in SEQ ID NO:3.

3. An isolated bacterium transfected with a vector, said bacterium selected from the group consisting of avirulent *C. sporogenes*, avirulent *C. beijerinckii*, and attenuated, non-pathogenic *S. typhimurium*, said vector comprising a recombinant nucleic acid sequence encoding thiaminase I from *N. gruberi* as set forth in SEQ ID NO:3, and said recombinant nucleic acid sequence operably linked to a promoter.

4. The bacterium of claim 3, wherein said bacterium is avirulent *C. sporogenes*.

5. The bacterium of claim 3, wherein said bacterium is avirulent *C. beijerinckii*.

6. The bacterium of claim 3, wherein said bacterium attenuated, non-pathogenic *S. typhimurium*.

* * * * *

SEQUENCE LISTING

<160> NUMBER OF SEQ ID NOS: 23

<210> SEQ ID NO 1
<211> LENGTH: 3078
<212> TYPE: DNA
<213> ORGANISM: Naegleria gruberi

<400> SEQUENCE: 1

```
atgtccactc aaccaaagac actcactgtt ggtctcttcc catatcttcc ttcttggaat      60
gaaaatggca acgaagttaa attgatcaat ttgatcaagg atgttttgcc aactcaggtt     120
tccggatata atatcgaata taccgaattt gattgttaca gtgatgctag tcttcaaagt     180
cttccagatg ttttctcaac tgatagcatt ttccttccat atcttgtttc tttgggtggt     240
gtcaagagtt tggatgaatc attggttcgt ggtgttactg tgatttgca tagttttgtt     300 tcctcaagtg cctctgtcaa tggttccgtt tatggtttcc cacaatactt gtgctcaaac     360
tttttattgt cctcaccaaa tggtactcaa caagcatctt ccctttttaga attggctcaa     420 aaggttggtt atgaacaaat tgtttatcca gatgttgcct cttctagttc tttcacagtt     480
ttcggattgt atcaacaatt actccaatca tcatcatcag ctgcagttga tatcaaggcc     540
tctgatcttc cacaatctgg tgaccaagtc aacaaggata tcactcaaaa atatagaacc     600
attttggatt caacagttgt tgcctctcaa agagaatata ttaactctgt aaagcaaggt     660
aaaccaattt caaactacta tgtcggatat agtgaaagta tgtgtgaaat taaggatatc     720
atcagagatc aacaatacaa tgttcaactc attggtacct ctgataagcc atacgtttat     780
actgatgttt tggctttgaa ttccaatttg tgtgatgaaa agcaaaaggt tgctgttgaa     840
gttatcaaga atttattgac taatacttta gttttggact tgttgggtct cggattaact     900
ctcccagcca acaagaatgg tattgctcat ttggctaaat catcaaactt ttatgctcaa     960
ttgagccaac aattcgatgc caaggaaagt gaagttagag ttttgagatg tgttgacttt    1020
gctaacaagg aagttaagaa ttgtgctggt gtcttgagac cattccttca acatattgct    1080
gttgctactt tgcgttgttt gactgctgac actgtcgaaa aggctaagag tggtcaccct    1140
ggtatgccaa ttggtatgtc accaattgcc tatgttttgt ggaagttctt cttcaaatca    1200
tctaaggatg atgtcaattg gttgaacaga gatagatttg ttttgagtaa tggtcacggt    1260
```

-continued

```
tgtacattgc tttatgccat gttgcacctc actgattgta acttgagttt ggatgatctc    1320
aagaatttca gaagtttgca ttccaagact cctggtcacc cagaatatgg tcacactgaa    1380
ggtgttgatg ctactactgg tccattgggt caaggtgttt gtaatgctat ggtatggct     1440 ctctctgaag ctcacttggc tgctcgtttc aataaggatg acaaaatat ctttgatcac     1500 cacacctatg ttttccttgg tgatggttgt tgatggaac gtgttgctat ggaaggtctc     1560
tcatttgctg gtcaccaaaa gttgaacaag ttgattgttt tctatgatga caatagtatt    1620
actattgatg gtaagactga attgaccttt actcaaaata ctccagaagt catgagaggt    1680
tttggatggc acgtaattgt tgtcgacaag gctgataatg acttggttgg tattaaggaa    1740
gctattttgg aagctcacac tgttactgac aagccaatca tgatcgtttg taagactaca    1800
attggttatt cctcaaaggt tcaaggtact gctaaggttc acggttctcc attgggtgct    1860
gatggattga agaatttgaa ggaaacttgt ggtttcactg gtaatgattt cttccatgtt    1920
ccagaaattg tcagaaagga cttgctact gtcattaata gaaatagtga aaagctctct     1980
caatggaagc aagttaaatc tgcctatgat accactcatg ctactgaatc ccaactcctc    2040
caaagaatga ttaatcacga attggaaggt gatgttatgg aaaagttgcc aaaataccct    2100
gaacaaaaga gattgctac cagatctaca tctcaacaag ttttgaatgc catctatcca    2160
ctcattcctt ctctcgttgg tggttcagct gacttgactc catccaactt gactgatgta    2220
actggatgtc aagatttcca accaaacaat agagttggta gatatatcag atttggtgtc    2280
cgtgaacatg ccatggttgc tattgccaat ggtattctct atcatggtgt tcttagaacc    2340
tatgttggta cattcttgaa ctttgcttca tatgctttgg gtgctatcag attgagtgcc    2400
ttgtctggtc ttccaaatat ttatgttttc actcatgaca gtattggtct tggtcaagat    2460
ggtccaactc accaacctgt tgaagtttta ccaatgttga tagccattcc aaatcacatt    2520
gttttcagac tgctgatgg tagagaaacc agtggtgctt atttgtgggc tgttcaatca    2580
aagaagactc catcctcaat gattctttct cgtcaagatt tgccacaatt gactggtact    2640
gatatttcaa aggttgcttt gggtgcctat gttatccaag gtgatgctac tcctgatgtt    2700
gtccttgttg gtactggttc tgaagtttcc ctcatggttg aagctgctga aaagttgaag    2760
gctaacctta aggttaacgt tgtttccatg ccaagtgggg aattgtttgt tcgtcaatca    2820
gaagaataca ggaagactgt cttcccagat ggtattccag ttgtcagtgc cgaagcttca    2880
tcaacctttg gttggacaag cttttgctcac tatgctgttg gtatgactac tttcggtgct    2940
agtgctgctg ctgaagaagt ttacaaactc ctcaagatta cctcagacaa tgttgctgaa    3000
aaggccacca aattggttac caagtatggt aagcaagctc caagactcag cttgtctctt    3060
gttggtgaag aactctaa                                                   3078
```

<210> SEQ ID NO 2
<211> LENGTH: 1025
<212> TYPE: PRT
<213> ORGANISM: Naegleria gruberi

<400> SEQUENCE: 2

Met Ser Thr Gln Pro Lys Thr Leu Thr Val Gly Leu Phe Pro Tyr Leu
 1               5                  10                  15

Pro Ser Trp Asn Glu Asn Gly Asn Glu Val Lys Leu Ile Asn Leu Ile
             20                  25                  30

Lys Asp Val Leu Pro Thr Gln Val Ser Gly Tyr Asn Ile Glu Tyr Thr
         35                  40                  45

-continued

```
Glu Phe Asp Cys Tyr Ser Asp Ala Ser Leu Gln Ser Leu Pro Asp Val
 50                  55                  60
Phe Ser Thr Asp Ser Ile Phe Leu Pro Tyr Leu Val Ser Leu Gly Gly
 65                  70                  75                  80
Val Lys Ser Leu Asp Glu Ser Leu Val Arg Gly Val Thr Gly Asp Leu
                 85                  90                  95
His Ser Phe Val Ser Ser Ser Ala Ser Val Asn Gly Ser Val Tyr Gly
                100                 105                 110
Phe Pro Gln Tyr Leu Cys Ser Asn Phe Leu Leu Ser Ser Pro Asn Gly
                115                 120                 125
Thr Gln Gln Ala Ser Ser Leu Leu Glu Leu Ala Gln Lys Val Gly Tyr
130                 135                 140
Glu Gln Ile Val Tyr Pro Asp Val Ala Ser Ser Ser Phe Thr Val
145                 150                 155                 160
Phe Gly Leu Tyr Gln Gln Leu Leu Gln Ser Ser Ser Ala Ala Val
                165                 170                 175
Asp Ile Lys Ala Ser Asp Leu Pro Gln Ser Gly Asp Gln Val Asn Lys
                180                 185                 190
Asp Ile Thr Gln Lys Tyr Arg Thr Ile Leu Asp Ser Thr Val Val Ala
                195                 200                 205
Ser Gln Arg Glu Tyr Ile Asn Ser Val Lys Gln Gly Lys Pro Ile Ser
210                 215                 220
Asn Tyr Tyr Val Gly Tyr Ser Glu Ser Met Cys Glu Ile Lys Asp Ile
225                 230                 235                 240
Ile Arg Asp Gln Gln Tyr Asn Val Gln Leu Ile Gly Thr Ser Asp Lys
                245                 250                 255
Pro Tyr Val Tyr Thr Asp Val Leu Ala Leu Asn Ser Asn Leu Cys Asp
                260                 265                 270
Glu Lys Gln Lys Val Ala Val Glu Val Ile Lys Asn Leu Leu Thr Asn
                275                 280                 285
Thr Leu Val Leu Asp Leu Leu Gly Leu Gly Leu Thr Leu Pro Ala Asn
290                 295                 300
Lys Asn Gly Ile Ala His Leu Ala Lys Ser Ser Asn Phe Tyr Ala Gln
305                 310                 315                 320
Leu Ser Gln Gln Phe Asp Ala Lys Glu Ser Glu Val Arg Val Leu Arg
                325                 330                 335
Cys Val Asp Phe Ala Asn Lys Glu Val Lys Asn Cys Ala Gly Val Leu
                340                 345                 350
Arg Pro Phe Leu Gln His Ile Ala Val Ala Thr Leu Arg Cys Leu Thr
                355                 360                 365
Ala Asp Thr Val Glu Lys Ala Lys Ser Gly His Pro Gly Met Pro Ile
370                 375                 380
Gly Met Ser Pro Ile Ala Tyr Val Leu Trp Lys Phe Phe Lys Ser
385                 390                 395                 400
Ser Lys Asp Asp Val Asn Trp Leu Asn Arg Asp Arg Phe Val Leu Ser
                405                 410                 415
Asn Gly His Gly Cys Thr Leu Leu Tyr Ala Met Leu His Leu Thr Asp
                420                 425                 430
Cys Asn Leu Ser Leu Asp Asp Leu Lys Asn Phe Arg Ser Leu His Ser
                435                 440                 445
Lys Thr Pro Gly His Pro Glu Tyr Gly His Thr Glu Gly Val Asp Ala
                450                 455                 460
Thr Thr Gly Pro Leu Gly Gln Gly Val Cys Asn Ala Ile Gly Met Ala
```

```
                465                 470                 475                 480
Leu Ser Glu Ala His Leu Ala Arg Phe Asn Lys Asp Gly Gln Asn
                    485                 490                 495

Ile Phe Asp His His Thr Tyr Val Phe Leu Gly Asp Gly Cys Leu Met
                500                 505                 510

Glu Arg Val Ala Met Glu Gly Leu Ser Phe Ala Gly His Gln Lys Leu
            515                 520                 525

Asn Lys Leu Ile Val Phe Tyr Asp Asp Asn Ser Ile Thr Ile Asp Gly
        530                 535                 540

Lys Thr Glu Leu Thr Phe Thr Gln Asn Thr Pro Glu Val Met Arg Gly
545                 550                 555                 560

Phe Gly Trp His Val Ile Val Val Asp Lys Ala Asp Asn Asp Leu Val
                565                 570                 575

Gly Ile Lys Glu Ala Ile Leu Glu Ala His Thr Val Thr Asp Lys Pro
            580                 585                 590

Ile Met Ile Val Cys Lys Thr Thr Ile Gly Tyr Ser Ser Lys Val Gln
        595                 600                 605

Gly Thr Ala Lys Val His Gly Ser Pro Leu Gly Ala Asp Gly Leu Lys
    610                 615                 620

Asn Leu Lys Glu Thr Cys Gly Phe Thr Gly Asn Asp Phe His Val
625                 630                 635                 640

Pro Glu Ile Val Arg Lys Asp Phe Ala Thr Val Ile Asn Arg Asn Ser
                645                 650                 655

Glu Lys Leu Ser Gln Trp Lys Gln Val Lys Ser Ala Tyr Asp Thr Thr
            660                 665                 670

His Ala Thr Glu Ser Gln Leu Leu Gln Arg Met Ile Asn His Glu Leu
        675                 680                 685

Glu Gly Asp Val Met Glu Lys Leu Pro Lys Tyr Leu Glu Gln Lys Lys
    690                 695                 700

Ile Ala Thr Arg Ser Thr Ser Gln Gln Val Leu Asn Ala Ile Tyr Pro
705                 710                 715                 720

Leu Ile Pro Ser Leu Val Gly Gly Ser Ala Asp Leu Thr Pro Ser Asn
                725                 730                 735

Leu Thr Asp Val Thr Gly Cys Gln Asp Phe Gln Pro Asn Asn Arg Val
            740                 745                 750

Gly Arg Tyr Ile Arg Phe Gly Val Arg Glu His Ala Met Val Ala Ile
        755                 760                 765

Ala Asn Gly Ile Leu Tyr His Gly Val Leu Arg Thr Tyr Val Gly Thr
    770                 775                 780

Phe Leu Asn Phe Ala Ser Tyr Ala Leu Gly Ala Ile Arg Leu Ser Ala
785                 790                 795                 800

Leu Ser Gly Leu Pro Asn Ile Tyr Val Phe Thr His Asp Ser Ile Gly
                805                 810                 815

Leu Gly Gln Asp Gly Pro Thr His Gln Pro Val Glu Val Leu Pro Met
            820                 825                 830

Leu Ile Ala Ile Pro Asn His Ile Val Phe Arg Pro Ala Asp Gly Arg
        835                 840                 845

Glu Thr Ser Gly Ala Tyr Leu Trp Ala Val Gln Ser Lys Lys Thr Pro
    850                 855                 860

Ser Ser Met Ile Leu Ser Arg Gln Asp Leu Pro Gln Leu Thr Gly Thr
865                 870                 875                 880

Asp Ile Ser Lys Val Ala Leu Gly Ala Tyr Val Ile Gln Gly Asp Ala
                885                 890                 895
```

```
Thr Pro Asp Val Val Leu Val Gly Thr Gly Ser Glu Val Ser Leu Met
            900                 905                 910

Val Glu Ala Ala Glu Lys Leu Lys Ala Asn Leu Lys Val Asn Val Val
            915                 920                 925

Ser Met Pro Ser Trp Glu Leu Phe Val Arg Gln Ser Glu Glu Tyr Arg
            930                 935                 940

Lys Thr Val Phe Pro Asp Gly Ile Pro Val Val Ser Ala Glu Ala Ser
945                 950                 955                 960

Ser Thr Phe Gly Trp Thr Ser Phe Ala His Tyr Ala Val Gly Met Thr
            965                 970                 975

Thr Phe Gly Ala Ser Ala Ala Glu Glu Val Tyr Lys Leu Leu Lys
            980                 985                 990

Ile Thr Ser Asp Asn Val Ala Glu Lys Ala Thr Lys Leu Val Thr Lys
            995                1000                1005

Tyr Gly Lys Gln Ala Pro Arg Leu Ser Leu Ser Leu Val Gly Glu Glu
        1010                1015                1020

Leu
1025

<210> SEQ ID NO 3
<211> LENGTH: 1068
<212> TYPE: DNA
<213> ORGANISM: Naegleria gruberi
<220> FEATURE:
<221> NAME/KEY: CDS
<222> LOCATION: (1)..(1068)

<400> SEQUENCE: 3
```

| | | | | | | | | | | | | | | | | |
|---|---|---|---|---|---|---|---|---|---|---|---|---|---|---|---|---|
| atg | tcc | act | caa | cca | aag | aca | ctc | act | gtt | ggt | ctc | ttc | cca | tat | ctt | 48 |
| Met | Ser | Thr | Gln | Pro | Lys | Thr | Leu | Thr | Val | Gly | Leu | Phe | Pro | Tyr | Leu | |
| 1 | | | | 5 | | | | | 10 | | | | | 15 | | |
| cct | tct | tgg | aat | gaa | aat | ggc | aac | gaa | gtt | aaa | ttg | atc | aat | ttg | atc | 96 |
| Pro | Ser | Trp | Asn | Glu | Asn | Gly | Asn | Glu | Val | Lys | Leu | Ile | Asn | Leu | Ile | |
| | | | 20 | | | | | 25 | | | | | 30 | | | |
| aag | gat | gtt | ttg | cca | act | cag | gtt | tcc | gga | tat | aat | atc | gaa | tat | acc | 144 |
| Lys | Asp | Val | Leu | Pro | Thr | Gln | Val | Ser | Gly | Tyr | Asn | Ile | Glu | Tyr | Thr | |
| | | 35 | | | | | 40 | | | | | 45 | | | | |
| gaa | ttt | gat | tgt | tac | agt | gat | gct | agt | ctt | caa | agt | ctt | cca | gat | gtt | 192 |
| Glu | Phe | Asp | Cys | Tyr | Ser | Asp | Ala | Ser | Leu | Gln | Ser | Leu | Pro | Asp | Val | |
| 50 | | | | | 55 | | | | | 60 | | | | | | |
| ttc | tca | act | gat | agc | att | ttc | ctt | cca | tat | ctt | gtt | tct | ttg | ggt | ggt | 240 |
| Phe | Ser | Thr | Asp | Ser | Ile | Phe | Leu | Pro | Tyr | Leu | Val | Ser | Leu | Gly | Gly | |
| 65 | | | | | 70 | | | | | 75 | | | | | 80 | |
| gtc | aag | agt | ttg | gat | gaa | tca | ttg | gtt | cgt | ggt | gtt | act | ggt | gat | ttg | 288 |
| Val | Lys | Ser | Leu | Asp | Glu | Ser | Leu | Val | Arg | Gly | Val | Thr | Gly | Asp | Leu | |
| | | | | 85 | | | | | 90 | | | | | 95 | | |
| cat | agt | ttt | gtt | tcc | tca | agt | gcc | tct | gtc | aat | ggt | tcc | gtt | tat | ggt | 336 |
| His | Ser | Phe | Val | Ser | Ser | Ser | Ala | Ser | Val | Asn | Gly | Ser | Val | Tyr | Gly | |
| | | | 100 | | | | | 105 | | | | | 110 | | | |
| ttc | cca | caa | tac | ttg | tgc | tca | aac | ttt | tta | ttg | tcc | tca | cca | aat | ggt | 384 |
| Phe | Pro | Gln | Tyr | Leu | Cys | Ser | Asn | Phe | Leu | Leu | Ser | Ser | Pro | Asn | Gly | |
| | | 115 | | | | | 120 | | | | | 125 | | | | |
| act | caa | caa | gca | tct | tcc | ctt | tta | gaa | ttg | gct | caa | aag | gtt | ggt | tat | 432 |
| Thr | Gln | Gln | Ala | Ser | Ser | Leu | Leu | Glu | Leu | Ala | Gln | Lys | Val | Gly | Tyr | |
| | 130 | | | | | 135 | | | | | 140 | | | | | |
| gaa | caa | att | gtt | tat | cca | gat | gtt | gcc | tct | tct | agt | tct | ttc | aca | gtt | 480 |
| Glu | Gln | Ile | Val | Tyr | Pro | Asp | Val | Ala | Ser | Ser | Ser | Phe | Thr | Val | |
| 145 | | | | | 150 | | | | | 155 | | | | | 160 | |

-continued

| | |
|---|---|
| ttc gga ttg tat caa caa tta ctc caa tca tca tca gct gca gtt<br>Phe Gly Leu Tyr Gln Gln Leu Leu Gln Ser Ser Ser Ala Ala Val<br>                165                    170                    175 | 528 |
| gat atc aag gcc tct gat ctt cca caa tct ggt gac caa gtc aac aag<br>Asp Ile Lys Ala Ser Asp Leu Pro Gln Ser Gly Asp Gln Val Asn Lys<br>        180                    185                    190 | 576 |
| gat atc act caa aaa tat aga acc att ttg gat tca aca gtt gtt gcc<br>Asp Ile Thr Gln Lys Tyr Arg Thr Ile Leu Asp Ser Thr Val Val Ala<br>                195                    200                    205 | 624 |
| tct caa aga gaa tat att aac tct gta aag caa ggt aaa cca att tca<br>Ser Gln Arg Glu Tyr Ile Asn Ser Val Lys Gln Gly Lys Pro Ile Ser<br>210                    215                    220 | 672 |
| aac tac tat gtc gga tat agt gaa agt atg tgt gaa att aag gat atc<br>Asn Tyr Tyr Val Gly Tyr Ser Glu Ser Met Cys Glu Ile Lys Asp Ile<br>225                    230                    235                    240 | 720 |
| atc aga gat caa caa tac aat gtt caa ctc att ggt acc tct gat aag<br>Ile Arg Asp Gln Gln Tyr Asn Val Gln Leu Ile Gly Thr Ser Asp Lys<br>                    245                    250                    255 | 768 |
| cca tac gtt tat act gat gtt ttg gct ttg aat tcc aat ttg tgt gat<br>Pro Tyr Val Tyr Thr Asp Val Leu Ala Leu Asn Ser Asn Leu Cys Asp<br>        260                    265                    270 | 816 |
| gaa aag caa aag gtt gct gtt gaa gtt atc aag aat tta ttg act aat<br>Glu Lys Gln Lys Val Ala Val Glu Val Ile Lys Asn Leu Leu Thr Asn<br>                275                    280                    285 | 864 |
| act tta gtt ttg gac ttg ttg ggt ctc gga tta act ctc cca gcc aac<br>Thr Leu Val Leu Asp Leu Leu Gly Leu Gly Leu Thr Leu Pro Ala Asn<br>290                    295                    300 | 912 |
| aag aat ggt att gct cat ttg gct aaa tca tca aac ttt tat gct caa<br>Lys Asn Gly Ile Ala His Leu Ala Lys Ser Ser Asn Phe Tyr Ala Gln<br>305                    310                    315                    320 | 960 |
| ttg agc caa caa ttc gat gcc aag gaa agt gaa gtt aga gtt ttg aga<br>Leu Ser Gln Gln Phe Asp Ala Lys Glu Ser Glu Val Arg Val Leu Arg<br>                    325                    330                    335 | 1008 |
| tgt gtt gac ttt gct aac aag gaa gtt aag aat tgt gct ggt gtc ttg<br>Cys Val Asp Phe Ala Asn Lys Glu Val Lys Asn Cys Ala Gly Val Leu<br>        340                    345                    350 | 1056 |
| aga cca ttc ctt<br>Arg Pro Phe Leu<br>        355 | 1068 |

<210> SEQ ID NO 4
<211> LENGTH: 356
<212> TYPE: PRT
<213> ORGANISM: Naegleria gruberi

<400> SEQUENCE: 4

Met Ser Thr Gln Pro Lys Thr Leu Thr Val Gly Leu Phe Pro Tyr Leu
1               5                   10                  15

Pro Ser Trp Asn Glu Asn Gly Asn Glu Val Lys Leu Ile Asn Leu Ile
                20                  25                  30

Lys Asp Val Leu Pro Thr Gln Val Ser Gly Tyr Asn Ile Glu Tyr Thr
            35                  40                  45

Glu Phe Asp Cys Tyr Ser Asp Ala Ser Leu Gln Ser Leu Pro Asp Val
        50                  55                  60

Phe Ser Thr Asp Ser Ile Phe Leu Pro Tyr Leu Val Ser Leu Gly Gly
65                  70                  75                  80

Val Lys Ser Leu Asp Glu Ser Leu Val Arg Gly Val Thr Gly Asp Leu
                85                  90                  95

His Ser Phe Val Ser Ser Ser Ala Ser Val Asn Gly Ser Val Tyr Gly

-continued

```
                100             105             110
Phe Pro Gln Tyr Leu Cys Ser Asn Phe Leu Ser Ser Pro Asn Gly
            115                 120                 125

Thr Gln Gln Ala Ser Ser Leu Leu Glu Leu Ala Gln Lys Val Gly Tyr
            130                 135                 140

Glu Gln Ile Val Tyr Pro Asp Val Ala Ser Ser Ser Phe Thr Val
145                 150                 155                 160

Phe Gly Leu Tyr Gln Gln Leu Leu Gln Ser Ser Ser Ala Ala Val
            165                 170                 175

Asp Ile Lys Ala Ser Asp Leu Pro Gln Ser Gly Asp Gln Val Asn Lys
            180                 185                 190

Asp Ile Thr Gln Lys Tyr Arg Thr Ile Leu Asp Ser Thr Val Ala
            195                 200                 205

Ser Gln Arg Glu Tyr Ile Asn Ser Val Lys Gln Gly Lys Pro Ile Ser
            210                 215                 220

Asn Tyr Tyr Val Gly Tyr Ser Glu Ser Met Cys Glu Ile Lys Asp Ile
225                 230                 235                 240

Ile Arg Asp Gln Gln Tyr Asn Val Gln Leu Ile Gly Thr Ser Asp Lys
            245                 250                 255

Pro Tyr Val Tyr Thr Asp Val Leu Ala Leu Asn Ser Asn Leu Cys Asp
            260                 265                 270

Glu Lys Gln Lys Val Ala Val Glu Val Ile Lys Asn Leu Leu Thr Asn
            275                 280                 285

Thr Leu Val Leu Asp Leu Leu Gly Leu Gly Leu Thr Leu Pro Ala Asn
            290                 295                 300

Lys Asn Gly Ile Ala His Leu Ala Lys Ser Ser Asn Phe Tyr Ala Gln
305                 310                 315                 320

Leu Ser Gln Gln Phe Asp Ala Lys Glu Ser Glu Val Arg Val Leu Arg
            325                 330                 335

Cys Val Asp Phe Ala Asn Lys Glu Val Lys Asn Cys Ala Gly Val Leu
            340                 345                 350

Arg Pro Phe Leu
            355

<210> SEQ ID NO 5
<211> LENGTH: 412
<212> TYPE: PRT
<213> ORGANISM: Saccharomyces cerevisiae

<400> SEQUENCE: 5

Ala Asp Asp Val Lys Gln Leu Lys Ser Lys Phe Gly Phe Asn Pro Asp
1               5                   10                  15

Lys Ser Phe Val Val Pro Gln Glu Val Tyr Asp His Tyr Gln Lys Thr
            20                  25                  30

Ile Leu Lys Pro Gly Val Glu Ala Asn Asn Lys Trp Asn Lys Leu Phe
            35                  40                  45

Ser Glu Tyr Gln Lys Lys Phe Pro Glu Leu Gly Ala Glu Leu Ala Arg
            50                  55                  60

Arg Leu Ser Gly Gln Leu Pro Ala Asn Trp Glu Ser Lys Leu Pro Thr
65                  70                  75                  80

Tyr Thr Ala Lys Asp Ser Ala Val Ala Thr Arg Lys Leu Ser Glu Thr
            85                  90                  95

Val Leu Glu Asp Val Tyr Asn Gln Leu Pro Glu Leu Ile Gly Gly Ser
            100                 105                 110
```

```
Ala Asp Leu Thr Pro Ser Asn Leu Thr Arg Trp Lys Glu Ala Leu Asp
        115                 120                 125

Phe Gln Pro Pro Ser Ser Gly Ser Gly Asn Tyr Ser Gly Arg Tyr Ile
130                 135                 140

Arg Tyr Gly Ile Arg Glu His Ala Met Gly Ala Ile Met Asn Gly Ile
145                 150                 155                 160

Ser Ala Phe Gly Ala Asn Tyr Lys Pro Tyr Gly Gly Thr Phe Leu Asn
                165                 170                 175

Phe Val Ser Tyr Ala Ala Gly Ala Val Arg Leu Ser Ala Leu Ser Gly
            180                 185                 190

His Pro Val Ile Trp Val Ala Thr His Asp Ser Ile Gly Val Gly Glu
        195                 200                 205

Asp Gly Pro Thr His Gln Pro Ile Glu Thr Leu Ala His Phe Arg Ser
    210                 215                 220

Leu Pro Asn Ile Gln Val Trp Arg Pro Ala Asp Gly Asn Glu Val Ser
225                 230                 235                 240

Ala Ala Tyr Lys Asn Ser Leu Glu Ser Lys His Thr Pro Ser Ile Ile
                245                 250                 255

Ala Leu Ser Arg Gln Asn Leu Pro Gln Leu Glu Gly Ser Ser Ile Glu
            260                 265                 270

Ser Ala Ser Lys Gly Gly Tyr Val Leu Gln Asp Val Ala Asn Pro Asp
        275                 280                 285

Ile Ile Leu Val Ala Thr Gly Ser Glu Val Ser Leu Ser Val Glu Ala
    290                 295                 300

Ala Lys Thr Leu Ala Ala Lys Asn Ile Lys Ala Arg Val Val Ser Leu
305                 310                 315                 320

Pro Asp Phe Phe Thr Phe Asp Lys Gln Pro Leu Glu Tyr Arg Leu Ser
                325                 330                 335

Val Leu Pro Asp Asn Val Pro Ile Met Ser Val Glu Val Leu Ala Thr
            340                 345                 350

Thr Cys Trp Gly Lys Tyr Ala His Gln Ser Phe Gly Ile Asp Arg Phe
        355                 360                 365

Gly Ala Ser Gly Lys Ala Pro Glu Val Phe Lys Phe Phe Gly Phe Thr
    370                 375                 380

Pro Glu Gly Val Ala Glu Arg Ala Gln Lys Thr Ile Ala Phe Tyr Lys
385                 390                 395                 400

Gly Asp Lys Leu Ile Ser Pro Leu Lys Lys Ala Phe
                405                 410

<210> SEQ ID NO 6
<211> LENGTH: 398
<212> TYPE: PRT
<213> ORGANISM: Craterostigma plantagineum

<400> SEQUENCE: 6

Pro Lys Glu Ala Glu Ala Thr Arg Lys Asn Leu Gly Trp Pro Tyr Glu
1               5                   10                  15

Pro Phe His Val Pro Asp Asp Val Lys Lys His Trp Ser Arg His Ile
                20                  25                  30

Ala Glu Gly Ala Ala Leu Glu Ser Ala Trp Asn Ala Lys Phe Ala Glu
            35                  40                  45

Phe Gln Lys Lys Phe Pro Glu Glu Ala Ala Asp Leu Lys Ser Ile Ile
        50                  55                  60

Thr Gly Glu Leu Pro Thr Asn Trp Glu Ser Ile Phe Pro Thr Tyr Thr
65                  70                  75                  80
```

Pro Glu Asn Pro Gly Leu Pro Thr Arg Thr Leu Ser His Gln Ile Leu
            85                  90                  95

Asn Gly Leu Gly Asp Val Leu Pro Gly Leu Leu Gly Gly Ser Ala Asp
            100                 105                 110

Leu Thr Leu Ser Asn Met Ala Phe Leu Lys Asn Ser Gly Asp Phe Gln
            115                 120                 125

Lys Lys Ser Pro Gly Glu Arg Asn Val Lys Phe Gly Ala Arg Glu His
            130                 135                 140

Ala Met Gly Ser Ile Cys Asn Gly Leu Ala Leu His Ser Pro Gly Leu
145                 150                 155                 160

Leu Pro Tyr Cys Ala Thr Tyr Phe Val Phe Thr Asp Tyr Met Arg Ala
                165                 170                 175

Ala Met Arg Ile Ser Ala Leu Ser Lys Ala Arg Val Leu Tyr Ile Met
            180                 185                 190

Thr His Asp Ser Ile Gly Leu Gly Glu Asp Gly Pro Thr His Gln Pro
            195                 200                 205

Val Glu His Leu Ala Ser Phe Arg Ala Met Pro Asn Ile Leu Thr Leu
            210                 215                 220

Arg Pro Ala Asp Gly Asn Glu Thr Ala Gly Ala Tyr Arg Ala Ala Val
225                 230                 235                 240

Gln Asn Gly Glu Arg Pro Ser Ile Leu Val Leu Ala Arg Gln Lys Leu
                245                 250                 255

Pro Gln Leu Pro Gly Thr Ser Ile Glu Gly Val Ser Lys Gly Gly Tyr
            260                 265                 270

Val Ile Ser Asp Asn Ser Arg Gly Gly Asn Ser Lys Pro Asp Val Ile
            275                 280                 285

Leu Ile Gly Thr Gly Ser Glu Leu Glu Ile Ala Ala Arg Ala Gly Asp
            290                 295                 300

Glu Leu Arg Lys Glu Gly Lys Lys Val Arg Val Val Ser Leu Val Cys
305                 310                 315                 320

Trp Glu Leu Phe Ala Glu Gln Ser Glu Lys Tyr Arg Glu Thr Val Leu
                325                 330                 335

Pro Ser Gly Val Thr Ala Arg Val Ser Val Glu Ala Gly Ser Thr Phe
            340                 345                 350

Gly Trp Glu Arg Phe Ile Gly Pro Lys Gly Lys Ala Val Gly Ile Asp
            355                 360                 365

Arg Phe Gly Ala Ser Ala Pro Ala Glu Arg Leu Phe Lys Glu Phe Gly
            370                 375                 380

Ile Thr Val Glu Ala Val Val Ala Ala Lys Glu Ile Cys
385                 390                 395

<210> SEQ ID NO 7
<211> LENGTH: 402
<212> TYPE: PRT
<213> ORGANISM: Escherichia coli

<400> SEQUENCE: 7

Glu Glu Glu Val Ala Leu Ala Arg Gln Lys Leu Gly Trp His His Pro
  1               5                  10                  15

Pro Phe Glu Ile Pro Lys Glu Ile Tyr His Ala Trp Asp Ala Arg Glu
             20                  25                  30

Lys Gly Glu Lys Ala Gln Gln Ser Trp Asn Glu Lys Phe Ala Ala Tyr
         35                  40                  45

Lys Lys Ala His Pro Gln Leu Ala Glu Glu Phe Thr Arg Arg Met Ser

Gly Gly Leu Pro Lys Asp Trp Glu Lys Thr Thr Gln Lys Tyr Ile Asn
65                  70                  75                  80

Glu Leu Gln Ala Asn Pro Ala Lys Ile Ala Thr Arg Lys Ala Ser Gln
                85                  90                  95

Asn Thr Leu Asn Ala Tyr Gly Pro Met Leu Pro Glu Leu Leu Gly Gly
            100                 105                 110

Ser Ala Asp Leu Ala Pro Ser Asn Leu Thr Ile Trp Lys Gly Ser Val
        115                 120                 125

Ser Leu Lys Glu Asp Pro Ala Gly Asn Tyr Ile His Tyr Gly Val Arg
    130                 135                 140

Glu Phe Gly Met Thr Ala Ile Ala Asn Gly Ile Ala His His Gly Gly
145                 150                 155                 160

Phe Val Pro Tyr Thr Ala Thr Phe Leu Met Phe Val Glu Tyr Ala Arg
            165                 170                 175

Asn Ala Ala Arg Met Ala Ala Leu Met Lys Ala Arg Gln Ile Met Val
        180                 185                 190

Tyr Thr His Asp Ser Ile Gly Leu Gly Glu Asp Gly Pro Thr His Gln
    195                 200                 205

Ala Val Glu Gln Leu Ala Ser Leu Arg Leu Thr Pro Asn Phe Ser Thr
210                 215                 220

Trp Arg Pro Cys Asp Gln Val Glu Ala Ala Val Gly Trp Lys Leu Ala
225                 230                 235                 240

Val Glu Arg His Asn Gly Pro Thr Ala Leu Ile Leu Ser Arg Gln Asn
            245                 250                 255

Leu Ala Gln Val Glu Arg Thr Pro Asp Gln Val Lys Glu Ile Ala Arg
        260                 265                 270

Gly Gly Tyr Val Leu Lys Asp Ser Gly Gly Lys Pro Asp Ile Ile Leu
    275                 280                 285

Ile Ala Thr Gly Ser Glu Met Glu Ile Thr Leu Gln Ala Ala Glu Lys
    290                 295                 300

Leu Ala Gly Glu Gly Arg Asn Val Arg Val Ser Leu Pro Ser Thr
305                 310                 315                 320

Asp Ile Phe Asp Ala Gln Asp Glu Glu Tyr Arg Glu Ser Val Leu Pro
            325                 330                 335

Ser Asn Val Ala Ala Arg Val Ala Val Glu Ala Gly Ile Ala Asp Tyr
        340                 345                 350

Trp Tyr Lys Tyr Val Gly Leu Lys Gly Ala Ile Val Gly Met Thr Gly
    355                 360                 365

Tyr Gly Glu Ser Ala Pro Ala Asp Lys Leu Phe Pro Phe Phe Gly Phe
    370                 375                 380

Thr Ala Glu Asn Ile Val Ala Lys Ala His Lys Val Leu Gly Val Lys
385                 390                 395                 400

Gly Ala

<210> SEQ ID NO 8
<211> LENGTH: 400
<212> TYPE: PRT
<213> ORGANISM: Bacillus subtilis

<400> SEQUENCE: 8

Lys Glu Glu Ser Lys Leu Thr Lys Glu Ala Tyr Ala Trp Thr Tyr Glu
1               5                   10                  15

Glu Asp Phe Tyr Val Pro Ser Glu Val Tyr Glu His Phe Ala Val Ala

```
                20                  25                  30
Val Lys Glu Ser Gly Glu Lys Glu Gln Glu Trp Asn Ala Gln Phe
             35                  40                  45
Ala Lys Tyr Lys Glu Val Tyr Pro Glu Leu Ala Glu Gln Leu Glu Leu
 50                  55                  60
Ala Ile Lys Gly Glu Leu Pro Lys Asp Trp Asp Gln Glu Val Pro Val
 65                  70                  75                  80
Tyr Glu Lys Gly Ser Ser Leu Ala Ser Arg Ala Ser Gly Glu Val
                 85                  90                  95
Leu Asn Gly Leu Ala Lys Lys Ile Pro Phe Phe Val Gly Gly Ser Ala
                100                 105                 110
Asp Leu Ala Gly Ser Asn Lys Thr Thr Ile Lys Asn Ala Gly Asp Phe
                115                 120                 125
Thr Ala Val Asp Tyr Ser Gly Lys Asn Phe Trp Phe Gly Val Arg Glu
                130                 135                 140
Phe Ala Met Gly Ala Ala Leu Asn Gly Met Ala Leu His Gly Gly Leu
145                 150                 155                 160
Arg Val Phe Gly Gly Thr Phe Phe Val Phe Ser Asp Tyr Leu Arg Pro
                165                 170                 175
Ala Ile Arg Leu Ala Ala Leu Met Gly Leu Pro Val Thr Tyr Val Phe
                180                 185                 190
Thr His Asp Ser Ile Ala Val Gly Glu Asp Gly Pro Thr His Glu Pro
                195                 200                 205
Val Glu Gln Leu Ala Ser Leu Arg Ala Met Pro Asn Leu Ser Leu Ile
                210                 215                 220
Arg Pro Ala Asp Gly Asn Glu Thr Ala Ala Trp Lys Leu Ala Val
225                 230                 235                 240
Gln Ser Thr Asp His Pro Thr Ala Leu Val Leu Thr Arg Gln Asn Leu
                245                 250                 255
Pro Thr Ile Asp Gln Thr Ser Glu Glu Ala Leu Ala Gly Val Glu Lys
                260                 265                 270
Gly Ala Tyr Val Val Ser Lys Ser Lys Asn Glu Thr Pro Asp Ala Leu
                275                 280                 285
Leu Ile Ala Ser Gly Ser Glu Val Gly Leu Ala Ile Glu Ala Gln Ala
                290                 295                 300
Glu Leu Ala Lys Glu Asn Ile Asp Val Ser Val Ser Met Pro Ser
305                 310                 315                 320
Met Asp Arg Phe Glu Lys Gln Ser Asp Glu Tyr Lys Asn Glu Val Leu
                325                 330                 335
Pro Ala Asp Val Lys Lys Arg Leu Ala Ile Glu Met Gly Ser Ser Phe
                340                 345                 350
Gly Trp Gly Lys Tyr Thr Gly Leu Glu Gly Asp Val Leu Gly Ile Asp
                355                 360                 365
Arg Phe Gly Ala Ser Ala Pro Gly Glu Thr Ile Ile Asn Glu Tyr Gly
                370                 375                 380
Phe Ser Val Pro Asn Val Val Asn Arg Val Lys Ala Leu Ile Asn Lys
385                 390                 395                 400

<210> SEQ ID NO 9
<211> LENGTH: 391
<212> TYPE: PRT
<213> ORGANISM: Mycoplasma genitalium

<400> SEQUENCE: 9
```

-continued

```
Glu Val Asp Phe Gln Leu Phe Glu Lys Arg Thr Asn Thr Asn Phe Asn
 1               5                  10                  15
Phe Phe Asn Tyr Pro Asp Ser Ile Tyr His Trp Phe Lys Gln Thr Val
                 20                  25                  30
Ile Glu Arg Gln Lys Gln Ile Lys Glu Asp Tyr Asn Asn Leu Leu Ile
             35                  40                  45
Ser Leu Lys Asp Lys Pro Leu Phe Lys Phe Thr Asn Trp Ile Asp
         50                  55                  60
Ser Asp Phe Gln Ala Leu Tyr Leu Asn Gln Leu Asp Glu Lys Lys Val
 65                  70                  75                  80
Ala Lys Lys Asp Ser Ala Thr Arg Asn Tyr Leu Lys Asp Phe Leu Asn
                 85                  90                  95
Gln Ile Asn Asn Pro Asn Ser Asn Leu Tyr Cys Leu Asn Ala Asp Val
             100                 105                 110
Ser Arg Ser Cys Phe Ile Lys Ile Gly Asp Asp Asn Leu His Glu Asn
         115                 120                 125
Pro Cys Ser Arg Asn Ile Gln Ile Gly Ile Arg Glu Phe Ala Met Ala
     130                 135                 140
Thr Ile Met Asn Gly Met Ala Leu His Gly Ile Lys Val Met Gly
145                 150                 155                 160
Gly Thr Phe Leu Ala Phe Ala Asp Tyr Ser Lys Pro Ala Ile Arg Leu
                 165                 170                 175
Gly Ala Leu Met Asn Leu Pro Val Phe Tyr Val Tyr Thr His Asp Ser
             180                 185                 190
Tyr Gln Val Gly Gly Asp Gly Pro Thr His Gln Pro Tyr Asp Gln Leu
         195                 200                 205
Pro Met Leu Arg Ala Ile Glu Asn Val Cys Val Phe Arg Pro Cys Asp
     210                 215                 220
Glu Lys Glu Thr Cys Ala Gly Phe Asn Tyr Gly Leu Leu Ser Gln Asp
225                 230                 235                 240
Gln Thr Thr Val Leu Val Leu Thr Arg Gln Pro Leu Lys Ser Ile Asp
                 245                 250                 255
Asn Thr Asp Ser Leu Lys Thr Leu Lys Gly Gly Tyr Ile Leu Leu Asp
             260                 265                 270
Arg Lys Gln Pro Asp Leu Ile Ile Ala Ala Ser Gly Ser Glu Val Gln
         275                 280                 285
Leu Ala Ile Glu Phe Glu Lys Val Leu Thr Lys Gln Asn Val Lys Val
     290                 295                 300
Arg Ile Leu Ser Val Pro Asn Ile Thr Leu Leu Lys Gln Asp Glu
305                 310                 315                 320
Lys Tyr Leu Lys Ser Leu Phe Asp Ala Asn Ser Ser Leu Ile Thr Ile
                 325                 330                 335
Glu Ala Ser Ser Ser Tyr Glu Trp Phe Cys Phe Lys Lys Tyr Val Lys
             340                 345                 350
Asn His Ala His Leu Gly Ala Phe Ser Phe Gly Glu Ser Asp Asp Gly
         355                 360                 365
Asp Lys Val Tyr Gln Gln Lys Gly Phe Asn Leu Glu Arg Leu Met Lys
     370                 375                 380
Ile Phe Thr Ser Leu Arg Asn
385                 390
```

<210> SEQ ID NO 10
<211> LENGTH: 316
<212> TYPE: PRT

<213> ORGANISM: Methanococcus jannaschii

<400> SEQUENCE: 10

| Met | Val | Lys | Leu | Ser | Gly | Val | Tyr | Lys | Gly | Met | Arg | Lys | Gly | Tyr | Gly |
|---|---|---|---|---|---|---|---|---|---|---|---|---|---|---|---|
| 1 | | | | 5 | | | | | 10 | | | | | 15 | |

Glu Thr Leu Ile Glu Leu Gly Lys Lys Tyr Glu Asn Leu Val Val Leu
                    20                  25                  30

Asp Ala Asp Leu Ser Gly Ser Thr Gln Thr Ala Met Phe Ala Lys Glu
                35                  40                  45

Phe Pro Glu Arg Phe Phe Asn Ala Gly Val Ala Glu Gln Asn Met Ile
        50                  55                  60

Gly Met Ala Ala Gly Leu Ala Thr Thr Gly Lys Ile Val Phe Ala Ser
65                  70                  75                  80

Ser Phe Ser Met Phe Ala Ser Gly Arg Ala Trp Glu Ile Ile Arg Asn
                85                  90                  95

Leu Val Ala Tyr Pro Lys Leu Asn Val Lys Ile Val Ala Thr His Ala
                    100                 105                 110

Gly Ile Thr Val Gly Glu Asp Gly Ala Ser His Gln Met Cys Glu Asp
                115                 120                 125

Ile Ala Ile Met Arg Ala Ile Pro Asn Met Val Val Ile Ala Pro Thr
130                 135                 140

Asp Tyr Tyr His Thr Lys Asn Val Ile Arg Thr Ile Ala Glu Tyr Lys
145                 150                 155                 160

Gly Pro Val Tyr Val Arg Met Pro Arg Arg Asp Thr Glu Ile Ile Tyr
                165                 170                 175

Glu Asn Glu Glu Glu Ala Thr Phe Glu Ile Gly Lys Gly Lys Ile Leu
                180                 185                 190

Val Asp Gly Glu Asp Leu Thr Ile Ile Ala Thr Gly Glu Glu Val Pro
            195                 200                 205

Glu Ala Leu Arg Ala Gly Glu Ile Leu Lys Glu Asn Gly Ile Ser Ala
            210                 215                 220

Glu Ile Val Glu Met Ala Thr Ile Lys Pro Ile Asp Glu Glu Ile Ile
225                 230                 235                 240

Lys Lys Ser Lys Asp Phe Val Val Thr Val Glu Asp His Ser Ile Ile
                245                 250                 255

Gly Gly Leu Gly Gly Ala Val Ala Glu Val Ile Ala Ser Asn Gly Leu
                260                 265                 270

Asn Lys Lys Leu Leu Arg Ile Gly Ile Asn Asp Val Phe Gly Arg Ser
            275                 280                 285

Gly Lys Ala Asp Glu Leu Leu Lys Tyr Tyr Gly Leu Asp Gly Glu Ser
        290                 295                 300

Ile Ala Lys Arg Ile Met Glu Glu Met Lys Lys Glu
305                 310                 315

<210> SEQ ID NO 11
<211> LENGTH: 409
<212> TYPE: PRT
<213> ORGANISM: Bacillus thiaminolyticus

<400> SEQUENCE: 11

Met Ser Lys Val Lys Gly Phe Ile Tyr Lys Pro Leu Met Val Met Leu
1               5                   10                  15

Ala Leu Leu Leu Val Val Val Ser Pro Ala Gly Ala Gly Ala Ala His
                20                  25                  30

Ser Asp Ala Ser Ser Asp Ile Thr Leu Lys Val Ala Ile Tyr Pro Tyr

```
                35                  40                  45
Val Pro Asp Pro Ala Arg Phe Gln Ala Ala Val Leu Asp Gln Trp Gln
 50                  55                  60

Arg Gln Glu Pro Gly Val Lys Leu Glu Phe Thr Asp Trp Asp Ser Tyr
 65                  70                  75                  80

Ser Ala Asp Pro Pro Asp Asp Leu Asp Val Phe Val Leu Asp Ser Ile
                 85                  90                  95

Phe Leu Ser His Phe Val Asp Ala Gly Tyr Leu Leu Pro Phe Gly Ser
                100                 105                 110

Gln Asp Ile Asp Gln Ala Glu Asp Val Leu Pro Phe Ala Leu Gln Gly
                115                 120                 125

Ala Lys Arg Asn Gly Glu Val Tyr Gly Leu Pro Gln Ile Leu Cys Thr
130                 135                 140

Asn Leu Leu Phe Tyr Arg Lys Gly Asp Leu Lys Ile Gly Gln Val Asp
145                 150                 155                 160

Asn Ile Tyr Glu Leu Tyr Lys Lys Ile Gly Thr Ser His Ser Glu Gln
                165                 170                 175

Ile Pro Pro Gln Asn Lys Gly Leu Leu Ile Asn Met Ala Gly Gly
                180                 185                 190

Thr Thr Lys Ala Ser Met Tyr Leu Glu Ala Leu Ile Asp Val Thr Gly
                195                 200                 205

Gln Tyr Thr Glu Tyr Asp Leu Leu Pro Pro Leu Asp Pro Leu Asn Asp
210                 215                 220

Lys Val Ile Arg Gly Leu Arg Leu Leu Ile Asn Met Ala Gly Glu Lys
225                 230                 235                 240

Pro Ser Gln Tyr Val Pro Glu Asp Gly Asp Ala Tyr Val Arg Ala Ser
                245                 250                 255

Trp Phe Ala Gln Gly Ser Gly Arg Ala Phe Ile Gly Tyr Ser Glu Ser
                260                 265                 270

Met Met Arg Met Gly Asp Tyr Ala Glu Gln Val Arg Phe Lys Pro Ile
                275                 280                 285

Ser Ser Ser Ala Gly Gln Asp Ile Pro Leu Phe Tyr Ser Asp Val Val
290                 295                 300

Ser Val Asn Ser Lys Thr Ala His Pro Glu Leu Ala Lys Lys Leu Ala
305                 310                 315                 320

Asn Val Met Ala Ser Ala Asp Thr Val Glu Gln Ala Leu Arg Pro Gln
                325                 330                 335

Ala Asp Gly Gln Tyr Pro Gln Tyr Leu Leu Pro Ala Arg His Gln Val
                340                 345                 350

Tyr Glu Ala Leu Met Gln Asp Tyr Pro Ile Tyr Ser Glu Leu Ala Gln
                355                 360                 365

Ile Val Asn Lys Pro Ser Asn Arg Val Phe Arg Leu Gly Pro Glu Val
                370                 375                 380

Arg Thr Trp Leu Lys Asp Ala Lys Gln Val Leu Pro Glu Ala Leu Gly
385                 390                 395                 400

Leu Thr Asp Val Ser Ser Leu Ala Ser
                405

<210> SEQ ID NO 12
<211> LENGTH: 13
<212> TYPE: PRT
<213> ORGANISM: Naegleria gruberi

<400> SEQUENCE: 12
```

```
Ala Ser Asp Leu Pro Gln Ser Gly Asp Gln Val Asn Lys
 1               5                  10
```

```
<210> SEQ ID NO 13
<211> LENGTH: 12
<212> TYPE: PRT
<213> ORGANISM: Naegleria gruberi

<400> SEQUENCE: 13
```

```
Thr Ile Leu Asp Ser Thr Val Val Ala Ser Gln Arg
 1               5                  10
```

```
<210> SEQ ID NO 14
<211> LENGTH: 15
<212> TYPE: PRT
<213> ORGANISM: Naegleria gruberi

<400> SEQUENCE: 14
```

```
Ser Ser Asn Phe Tyr Ala Gln Leu Ser Gln Gln Phe Asp Ala Lys
 1               5                  10                  15
```

```
<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Primer

<400> SEQUENCE: 15
```

```
Cys Ala Arg Trp Ser Ile Gly Gly His Gly Ala Tyr Cys Ala Arg Gly
 1               5                  10                  15
```

```
<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Primer

<400> SEQUENCE: 16
```

```
Thr Thr Ile Gly Cys Arg Thr Cys Arg Ala Ala Tyr Thr Gly Tyr Thr
 1               5                  10                  15

Gly
```

```
<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 17
tgtcggatat agtgaaagta tg                                              22
```

```
<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 18 aacctttgc ttttcatcac ac                                               22
```

```
<210> SEQ ID NO 19
```

-continued

```
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 19
gagatataca tatgtccact caaccaaaga c                                 31

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 20
tatggatcct taaaggaatg gtctcaagac acc                               33

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 21
caataaaaag tttgagctca agtattg                                      27

<210> SEQ ID NO 22
<211> LENGTH: 13
<212> TYPE: PRT
<213> ORGANISM: Naegleria gruberi

<400> SEQUENCE: 22

Val Tyr Gly Phe Pro Gln Tyr Leu Cys Ser Asn Phe Leu
  1               5                  10

<210> SEQ ID NO 23
<211> LENGTH: 6
<212> TYPE: PRT
<213> ORGANISM: Naegleria gruberi

<400> SEQUENCE: 23

Gly Tyr Ser Glu Ser Met
  1               5
```